(12) United States Patent
Sokoloff et al.

(10) Patent No.: US 6,872,519 B1
(45) Date of Patent: Mar. 29, 2005

(54) IN VITRO PROCESS FOR SELECTING PHAGE RESISTANT TO BLOOD INACTIVATION

(75) Inventors: Alexander V. Sokoloff, Madison, WI (US); Jon A. Wolff, Madison, WI (US)

(73) Assignee: Mirus Bio Corporation, Madison, WI (US)

(*) Notice: Subject to any disclaimer, the term of this patent is extended or adjusted under 35 U.S.C. 154(b) by 0 days.

(21) Appl. No.: 09/559,021

(22) Filed: Apr. 27, 2000

Related U.S. Application Data

(60) Provisional application No. 60/139,431, filed on Jun. 7, 1999, and provisional application No. 60/131,151, filed on Apr. 27, 1999.

(51) Int. Cl.[7] .......................... C12Q 1/68; C12Q 1/70; C12N 7/00; A61K 49/00; C07H 21/04
(52) U.S. Cl. .................. 435/5; 435/6; 435/7.1; 435/235.1; 435/320.1; 536/23.1; 514/2; 514/44; 424/9.1
(58) Field of Search ................. 435/5, 6, 7.1, 320.1, 435/235.1; 536/23.1; 514/2, 44; 424/9.1, 9.34

(56) References Cited

U.S. PATENT DOCUMENTS 5,811,093 A * 9/1998 Merril et al. ............... 424/93.6

OTHER PUBLICATIONS

Sahu, et al. "Inhibition of human complement by a C3–binding peptide isolated from a phage–displayed random peptide library." Journal of Immunology, vol. 157, No. 2, pp. 884–891, 1996.*
The 1997 Novagen Catalog, pp. 24–26. Novagen Inc., 601 Science Drive, Madison, WI 53711.*
Arap, W. Et al., "Cancer Treatment By Targeted Drug Delivery to Tumor Vascultature in a Mouse Model." *Science*; Jan. 16, 1998; vol. 279; 377–380.
Barinaga, Marcia, "Cancer Research: Peptide–Guided Cancer Drugs Show Promise in Mice." *Science Magazine*; Jan. 16, 1998; vol. 279 No. 5349; 323–324.
Bohn, Jorg, "Are Natural Antibodies Involved in Tumour Defence?" *Immunology Letters*; 1999; vol. 69; 317–320.
Bouvet, Jean–Pierre, Et al., "From Natural Polyreactive Autoauntibodies to A La Carte Monoreactive Antibodies to Infectious Agents: Is It a Small World After All?" *Infection and Immunity*; Jan. 1998, vol. 66, No. 1; 1–4.
Casali, P. Et al., "Structure and Function of Natural Antibodies." *Current Topics in Microbiology & Immunology*; v.210 Pp. 167–179 (1996).
Clackson, Tim, Et al., "Making Antibody Fragments Using Phage Display Libraries." *Nature*; Aug. 15, 1991, vol. 352, pp. 624–628.
Dighiero, G., "Natural Autoantibodies, Tolerance, and Autoimmunity." *Annals New York Academy of Sciences*; 183–192.

Folkman, Judah, "Addressing Tumor Blood Vessels." *Nature Biotechnology*; Jun. 97; vol. 15; 510.
Healy, Kevin E. Et al., "Designing Biomaterials to Direct Biological Responses." *Annals New York Academy of Sciences*; pp. 24–35.
Ivanenkov, Vasily, Et al., "Targeted Delivery of Multivalent Phage Display Vectors Into Mammalian Cells." *Biochemica et Biophysica Acta*; 1999, vol. 1448; 463–472.
Ivanenkov, Vasily, Et al., "Uptake and Intracellular Fate of Phage Display Vectors in Mammalian Cells." *Biochemica et Biophysica Acta*; 1999, vol. 1448; 450–462.
Kassner, Paul D, Et al., "Genetic Selection of Phage Engineered for Receptor–Mediated Gene Transfer to Mammalian Cells." *Biochemical and Biophysical Research Communications*; 1999, vol. 264; 921–928.
Koivunen, Erkki Et al., "Tumor Targeting With a Selective Gelatinase Inhibitor." *Nature Biotechnology*; Aug. 99; vol. 17; 768–774.
Koivunen, Erkki, Et al., "Identification of Receptor Ligands with Phage Display Peptide Libraries." *The Journal of Nuclear Medicine*; May 1999; vol. 40, No. 5; 883–888.
Lacroix–Desmazes, Sebastien, Et al., "Self–Reactive Antibodies (Natural Autoantibodies) in Healthy Individuals." *Journal of Immunological Methods*; 1998; vol. 216; 117–137.
McCafferty, John, Et al., "Phage Antibodies: Filamentous Phage Displaying Antibody Variable Domains." *Nature*; Dec. 6, 1990; vol. 348; 552–554.
Merril, Carl R. Et al., "Long–Circulating Bacteriophage as Antibacterial Agents." *Proc. Natl. Acad. Sci. USA*; Apr. 1996; vol. 93; pp. 3188–3192.
Pasqualini, Renata Et al., "Integrins as Receptors For Tumor Targeting By Circulating Ligands." *Nature Biotechnology*; Jun. 97; vol. 15; 542–546.
Pasqualini, Renata, Et al., "Organ Targeting In Vivo Using Phage Display Peptide Libraries." *Nature*; Mar. 28, 1996; vol. 380; 364–366.
Rajotte, Daniel, Et al., "Membrane Dipeptidase Is the Receptor for a Lung–Targeting Peptide Identified by In Vivo Phage Display." *The Journal of Biological Chemistry*; Apr. 23, 1999; vol. 274, No. 17; 11593–11598.
Rajotte, Daniel, Et al., "Molecular Heterogeneity of the Vascular Endothelium Revealed by In Vivo Phage Display." *J. Clin. Invest.*; Jul. 1998; vol. 102, No. 2; 430–437.
Samoylova, Tatiana I. Et al., "Elucidation of Muscle–Binding Peptides by Phage Display Screening." *Muscle & Nerve*; Apr. 1999; 460–466.

* cited by examiner

*Primary Examiner*—Gerry Leffers
(74) *Attorney, Agent, or Firm*—Mark K. Johnson

(57) ABSTRACT

The present invention relates to compositions and methods for the selection and use of surface exposed epitopes. The present invention includes in vivo and in vitro phage peptide diplay methods for the identification and selection of peptides and peptide associated factors with desired properties (e.g., targeting specificity, stability, etc.). The present invention further provides methods and compositions for the isolation and identification of peptide-specific antibodies. The present invention also includes methods and compositions employing nuclear localization signals for enhanced nuclear transport and expression of DNA.

4 Claims, 1 Drawing Sheet

SEQUENCE LISTING

<160> NUMBER OF SEQ ID NOS: 125

<210> SEQ ID NO 1
<211> LENGTH: 11
<212> TYPE: PRT
<213> ORGANISM: Bacteriophage T7

<400> SEQUENCE: 1

Phe Gln Ser Gly Val Met Leu Gly Asp Pro Asn
1               5                   10

<210> SEQ ID NO 2
<211> LENGTH: 27
<212> TYPE: PRT
<213> ORGANISM: Bacteriophage T7

-continued

```
<400> SEQUENCE: 2

Phe Gln Ser Gly Val Met Leu Gly Asp Pro Asn Ser Asp Gly Ala Leu
1               5                   10                  15

Arg Gln Ser Gly Arg Gly Lys Ser Ser Arg Pro
            20                  25

<210> SEQ ID NO 3
<211> LENGTH: 23
<212> TYPE: PRT
<213> ORGANISM: Bacteriophage T7

<400> SEQUENCE: 3

Phe Gln Ser Gly Val Met Leu Gly Asp Pro Asn Ser Ser Ser Val Asp
1               5                   10                  15

Lys Leu Ala Ala Ala Leu Glu
            20

<210> SEQ ID NO 4
<211> LENGTH: 8
<212> TYPE: PRT
<213> ORGANISM: Bacteriophage T7

<400> SEQUENCE: 4

Ala Ala Gly Ala Val Val Phe Gln
1               5

<210> SEQ ID NO 5
<211> LENGTH: 343
<212> TYPE: PRT
<213> ORGANISM: Bacteriophage T7

<400> SEQUENCE: 5

Met Ala Ser Met Thr Gly Gly Gln Gln Met Gly Thr Asn Gln Gly Lys
1               5                   10                  15

Gly Val Val Ala Ala Gly Asp Lys Leu Ala Leu Phe Leu Lys Val Phe
            20                  25                  30

Gly Gly Glu Val Leu Thr Ala Phe Ala Arg Thr Ser Val Thr Thr Ser
        35                  40                  45

Arg His Met Val Arg Ser Ile Ser Ser Gly Lys Ser Ala Gln Phe Pro
    50                  55                  60

Val Leu Gly Arg Thr Gln Ala Ala Tyr Leu Ala Pro Gly Glu Asn Leu
65                  70                  75                  80

Asp Asp Lys Arg Lys Asp Ile Lys His Thr Glu Lys Val Ile Thr Ile
                85                  90                  95

Asp Gly Leu Leu Thr Ala Asp Val Leu Ile Tyr Asp Ile Glu Asp Ala
            100                 105                 110

Met Asn His Tyr Asp Val Arg Ser Glu Tyr Thr Ser Gln Leu Gly Glu
        115                 120                 125

Ser Leu Ala Met Ala Ala Asp Gly Ala Val Leu Ala Glu Ile Ala Gly
    130                 135                 140

Leu Cys Asn Val Glu Ser Lys Tyr Asn Glu Asn Ile Glu Gly Leu Gly
145                 150                 155                 160

Thr Ala Thr Val Ile Glu Thr Thr Gln Asn Lys Ala Ala Leu Thr Asp
                165                 170                 175

Gln Val Ala Leu Gly Lys Glu Ile Ile Ala Ala Leu Thr Lys Ala Arg
            180                 185                 190

Ala Ala Leu Thr Lys Asn Tyr Val Pro Ala Ala Asp Arg Val Phe Tyr
        195                 200                 205
```

```
Cys Asp Pro Asp Ser Tyr Ser Ala Ile Leu Ala Ala Leu Met Pro Asn
    210                 215                 220

Ala Ala Asn Tyr Ala Ala Leu Ile Asp Pro Glu Lys Gly Ser Ile Arg
225                 230                 235                 240

Asn Val Met Gly Phe Glu Val Val Glu Val Pro His Leu Thr Ala Gly
                245                 250                 255

Gly Ala Gly Thr Ala Arg Glu Gly Thr Thr Gly Gln Lys His Val Phe
                260                 265                 270

Pro Ala Asn Lys Gly Glu Gly Asn Val Lys Val Ala Lys Asp Asn Val
            275                 280                 285

Ile Gly Leu Phe Met His Arg Ser Ala Val Gly Thr Val Lys Leu Arg
    290                 295                 300

Asp Leu Ala Leu Glu Arg Ala Arg Arg Ala Asn Phe Gln Ala Asp Gln
305                 310                 315                 320

Ile Ile Ala Lys Tyr Ala Met Gly His Gly Gly Leu Arg Pro Glu Ala
                325                 330                 335

Ala Gly Ala Val Val Phe Gln
            340
```

<210> SEQ ID NO 6
<211> LENGTH: 9
<212> TYPE: PRT
<213> ORGANISM: Bacteriophage T7

<400> SEQUENCE: 6

```
Ala Ala Gly Ala Val Val Phe Gln Ser
1               5
```

<210> SEQ ID NO 7
<211> LENGTH: 10
<212> TYPE: PRT
<213> ORGANISM: Bacteriophage T7

<400> SEQUENCE: 7

```
Ala Ala Gly Ala Val Val Phe Ser Gln Val
1               5                   10
```

<210> SEQ ID NO 8
<211> LENGTH: 9
<212> TYPE: PRT
<213> ORGANISM: Bacteriophage T7

<400> SEQUENCE: 8

```
Glu Ala Ala Gly Ala Val Val Phe Gln
1               5
```

<210> SEQ ID NO 9
<211> LENGTH: 13
<212> TYPE: PRT
<213> ORGANISM: phage SV40

<400> SEQUENCE: 9

```
Cys Gly Tyr Gly Pro Lys Lys Lys Arg Lys Val Gly Gly
1               5                   10
```

<210> SEQ ID NO 10
<211> LENGTH: 39
<212> TYPE: PRT
<213> ORGANISM: phage SV40

```
<400> SEQUENCE: 10

Cys Lys Lys Lys Ser Ser Ser Asp Asp Glu Ala Thr Ala Asp Ser Gln
1               5                   10                  15

His Ser Thr Pro Pro Lys Lys Arg Lys Val Glu Asp Pro Lys Asp
                20                  25                  30

Phe Pro Ser Glu Leu Leu Ser
            35

<210> SEQ ID NO 11
<211> LENGTH: 38
<212> TYPE: PRT
<213> ORGANISM: phage SV40

<400> SEQUENCE: 11

Cys Lys Lys Lys Trp Asp Asp Asp Glu Ala Thr Ala Asp Ser Gln His
1               5                   10                  15

Ser Thr Pro Pro Lys Lys Lys Arg Lys Val Glu Asp Pro Lys Asp Phe
                20                  25                  30

Pro Ser Glu Leu Leu Ser
            35

<210> SEQ ID NO 12
<211> LENGTH: 32
<212> TYPE: PRT
<213> ORGANISM: M9 Protein

<400> SEQUENCE: 12

Cys Tyr Asn Asp Phe Gly Asn Tyr Asn Asn Gln Ser Ser Asn Phe Gly
1               5                   10                  15

Pro Met Lys Gln Gly Gly Asn Phe Gly Gly Arg Ser Ser Gly Pro Tyr
                20                  25                  30

<210> SEQ ID NO 13
<211> LENGTH: 10
<212> TYPE: PRT
<213> ORGANISM: E1A Adenovirus

<400> SEQUENCE: 13

Cys Lys Arg Gly Pro Lys Arg Pro Arg Pro
1               5                   10

<210> SEQ ID NO 14
<211> LENGTH: 22
<212> TYPE: PRT
<213> ORGANISM: Nucleoplasmin

<400> SEQUENCE: 14

Cys Lys Lys Ala Val Lys Arg Pro Ala Ala Thr Lys Lys Ala Gly Gln
1               5                   10                  15

Ala Lys Lys Lys Lys Leu
                20

<210> SEQ ID NO 15
<211> LENGTH: 14
<212> TYPE: PRT
<213> ORGANISM: c-myc

<400> SEQUENCE: 15

Cys Lys Lys Lys Gly Pro Ala Ala Lys Arg Val Lys Leu Asp
1               5                   10
```

```
<210> SEQ ID NO 16
<211> LENGTH: 4
<212> TYPE: PRT
<213> ORGANISM: Bacteriophage T7

<400> SEQUENCE: 16

Phe Ser Gln Val
1

<210> SEQ ID NO 17
<211> LENGTH: 4
<212> TYPE: PRT
<213> ORGANISM: endoplasmic reticulum proteins

<400> SEQUENCE: 17

Lys Asp Glu Leu
1

<210> SEQ ID NO 18
<211> LENGTH: 4
<212> TYPE: PRT
<213> ORGANISM: Bacteriophage T7

<400> SEQUENCE: 18

Gln Val Thr Lys
1

<210> SEQ ID NO 19
<211> LENGTH: 8
<212> TYPE: PRT
<213> ORGANISM: Bacteriophage T7

<400> SEQUENCE: 19

Val Val Val Glu Ser Val Pro Lys
1               5

<210> SEQ ID NO 20
<211> LENGTH: 6
<212> TYPE: PRT
<213> ORGANISM: Bacteriophage T7

<400> SEQUENCE: 20

Ala Arg Pro Val Gln Lys
1               5

<210> SEQ ID NO 21
<211> LENGTH: 8
<212> TYPE: PRT
<213> ORGANISM: Bacteriophage T7

<400> SEQUENCE: 21

Gln Leu Val Arg Val Ile Ser Arg
1               5

<210> SEQ ID NO 22
<211> LENGTH: 4
<212> TYPE: PRT
<213> ORGANISM: Bacteriophage T7

<400> SEQUENCE: 22

Gly Arg Leu Lys
1
```

```
<210> SEQ ID NO 23
<211> LENGTH: 5
<212> TYPE: PRT
<213> ORGANISM: Bacteriophage T7

<400> SEQUENCE: 23

Ala Phe Thr Asn Lys
1               5

<210> SEQ ID NO 24
<211> LENGTH: 6
<212> TYPE: PRT
<213> ORGANISM: Bacteriophage T7

<400> SEQUENCE: 24

Val Thr Pro Gln Val Lys
1               5

<210> SEQ ID NO 25
<211> LENGTH: 7
<212> TYPE: PRT
<213> ORGANISM: Bacteriophage T7

<400> SEQUENCE: 25

Asp Asn Thr Pro Lys Thr Lys
1               5

<210> SEQ ID NO 26
<211> LENGTH: 12
<212> TYPE: PRT
<213> ORGANISM: Bacteriophage T7

<400> SEQUENCE: 26

His Arg Pro Lys Glu Gly Gly Lys Pro Ala Leu Lys
1               5                   10

<210> SEQ ID NO 27
<211> LENGTH: 7
<212> TYPE: PRT
<213> ORGANISM: Bacteriophage T7

<400> SEQUENCE: 27

Arg Thr Asn Pro Lys Val Lys
1               5

<210> SEQ ID NO 28
<211> LENGTH: 6
<212> TYPE: PRT
<213> ORGANISM: Bacteriophage T7

<400> SEQUENCE: 28

Thr Thr Arg Thr Pro Lys
1               5

<210> SEQ ID NO 29
<211> LENGTH: 9
<212> TYPE: PRT
<213> ORGANISM: Bacteriophage T7

<400> SEQUENCE: 29

Asn Asn Ala Gln Gly Ala Arg Val Lys
1               5
```

-continued

```
<210> SEQ ID NO 30
<211> LENGTH: 5
<212> TYPE: PRT
<213> ORGANISM: Bacteriophage T7

<400> SEQUENCE: 30

Met Ala Thr Val Lys
1               5

<210> SEQ ID NO 31
<211> LENGTH: 5
<212> TYPE: PRT
<213> ORGANISM: Bacteriophage T7

<400> SEQUENCE: 31

Lys Leu Arg Met Lys
1               5

<210> SEQ ID NO 32
<211> LENGTH: 6
<212> TYPE: PRT
<213> ORGANISM: Bacteriophage T7

<400> SEQUENCE: 32

Gly Val Arg Glu Pro Lys
1               5

<210> SEQ ID NO 33
<211> LENGTH: 4
<212> TYPE: PRT
<213> ORGANISM: Bacteriophage T7

<400> SEQUENCE: 33

Pro Thr Ile Lys
1

<210> SEQ ID NO 34
<211> LENGTH: 10
<212> TYPE: PRT
<213> ORGANISM: Bacteriophage T7

<400> SEQUENCE: 34

Ser Arg Ala Ser Val Lys Gly Ser Thr Lys
1               5                   10

<210> SEQ ID NO 35
<211> LENGTH: 5
<212> TYPE: PRT
<213> ORGANISM: Bacteriophage T7

<400> SEQUENCE: 35

Arg Lys Pro Gln Lys
1               5

<210> SEQ ID NO 36
<211> LENGTH: 5
<212> TYPE: PRT
<213> ORGANISM: Bacteriophage T7

<400> SEQUENCE: 36

Lys Val Arg Glu Lys
1               5
```

```
<210> SEQ ID NO 37
<211> LENGTH: 5
<212> TYPE: PRT
<213> ORGANISM: Bacteriophage T7

<400> SEQUENCE: 37

Ala Ser Arg Val Arg
1               5

<210> SEQ ID NO 38
<211> LENGTH: 8
<212> TYPE: PRT
<213> ORGANISM: Bacteriophage T7

<400> SEQUENCE: 38

Lys Ser Gly Gly Pro Ala Glu Arg
1               5

<210> SEQ ID NO 39
<211> LENGTH: 7
<212> TYPE: PRT
<213> ORGANISM: Bacteriophage T7

<400> SEQUENCE: 39

Arg Arg Arg Asn Phe Glu Arg
1               5

<210> SEQ ID NO 40
<211> LENGTH: 13
<212> TYPE: PRT
<213> ORGANISM: Bacteriophage T7

<400> SEQUENCE: 40

Met Asp Ser Met Ser Asn Thr Pro Asn Gly Ser Glu Arg
1               5                   10

<210> SEQ ID NO 41
<211> LENGTH: 8
<212> TYPE: PRT
<213> ORGANISM: Bacteriophage T7

<400> SEQUENCE: 41

Pro Ser Ser Gln Gln Ala Gln Arg
1               5

<210> SEQ ID NO 42
<211> LENGTH: 4
<212> TYPE: PRT
<213> ORGANISM: Bacteriophage T7

<400> SEQUENCE: 42

Lys Asn Met Arg
1

<210> SEQ ID NO 43
<211> LENGTH: 5
<212> TYPE: PRT
<213> ORGANISM: Bacteriophage T7

<400> SEQUENCE: 43

Arg Lys Ser Leu Arg
1               5
```

```
<210> SEQ ID NO 44
<211> LENGTH: 5
<212> TYPE: PRT
<213> ORGANISM: Bacteriophage T7

<400> SEQUENCE: 44

Ile Glu Phe Ser Gly
1               5

<210> SEQ ID NO 45
<211> LENGTH: 10
<212> TYPE: PRT
<213> ORGANISM: Bacteriophage T7

<400> SEQUENCE: 45

Met Val Leu Pro Phe Gln Gln Thr Val Ala
1               5                   10

<210> SEQ ID NO 46
<211> LENGTH: 5
<212> TYPE: PRT
<213> ORGANISM: Bacteriophage T7

<400> SEQUENCE: 46

Gln Ser Ala Asn Ile
1               5

<210> SEQ ID NO 47
<211> LENGTH: 4
<212> TYPE: PRT
<213> ORGANISM: Bacteriophage T7

<400> SEQUENCE: 47

Lys Ile Pro Tyr
1

<210> SEQ ID NO 48
<211> LENGTH: 5
<212> TYPE: PRT
<213> ORGANISM: Bacteriophage T7

<400> SEQUENCE: 48

Leu Pro Ser Gly Gly
1               5

<210> SEQ ID NO 49
<211> LENGTH: 8
<212> TYPE: PRT
<213> ORGANISM: Bacteriophage T7

<400> SEQUENCE: 49

Tyr Asn Ala Lys Thr Asp Arg Gly
1               5

<210> SEQ ID NO 50
<211> LENGTH: 9
<212> TYPE: PRT
<213> ORGANISM: Bacteriophage T7

<400> SEQUENCE: 50

Lys Thr Asn Val Glu Lys Gly Pro Met
1               5
```

```
<210> SEQ ID NO 51
<211> LENGTH: 9
<212> TYPE: PRT
<213> ORGANISM: Bacteriophage T7

<400> SEQUENCE: 51

Asn Ser Asn Ala Gly Leu Glu Asn His
1               5

<210> SEQ ID NO 52
<211> LENGTH: 5
<212> TYPE: PRT
<213> ORGANISM: Bacteriophage T7

<400> SEQUENCE: 52

Met Val Arg Arg Val
1               5

<210> SEQ ID NO 53
<211> LENGTH: 6
<212> TYPE: PRT
<213> ORGANISM: Bacteriophage T7

<400> SEQUENCE: 53

Leu Ser Ala Arg Ala Pro
1               5

<210> SEQ ID NO 54
<211> LENGTH: 4
<212> TYPE: PRT
<213> ORGANISM: Bacteriophage T7

<400> SEQUENCE: 54

Arg Ser Tyr Arg
1

<210> SEQ ID NO 55
<211> LENGTH: 13
<212> TYPE: PRT
<213> ORGANISM: Bacteriophage T7

<400> SEQUENCE: 55

Gln Glu Ser Arg Thr Glu Thr Asp Ser Gln Tyr Leu Ala
1               5                   10

<210> SEQ ID NO 56
<211> LENGTH: 5
<212> TYPE: PRT
<213> ORGANISM: Bacteriophage T7

<400> SEQUENCE: 56

Gln Gly Asp Tyr Thr
1               5

<210> SEQ ID NO 57
<211> LENGTH: 4
<212> TYPE: PRT
<213> ORGANISM: Bacteriophage T7

<400> SEQUENCE: 57

Met Gln Tyr Ser
1
```

```
<210> SEQ ID NO 58
<211> LENGTH: 5
<212> TYPE: PRT
<213> ORGANISM: Bacteriophage T7

<400> SEQUENCE: 58

Tyr Gly Pro Gln Gln
1               5

<210> SEQ ID NO 59
<211> LENGTH: 14
<212> TYPE: PRT
<213> ORGANISM: Bacteriophage T7

<400> SEQUENCE: 59

Gly Lys Gly Lys Thr Asp Asp Pro Arg Tyr Gln Lys Phe Thr
1               5                   10

<210> SEQ ID NO 60
<211> LENGTH: 13
<212> TYPE: PRT
<213> ORGANISM: Bacteriophage T7

<400> SEQUENCE: 60

Ala Ala Thr Gly Ser Asp Gln Gly Leu Asn Lys Ala Tyr
1               5                   10

<210> SEQ ID NO 61
<211> LENGTH: 8
<212> TYPE: PRT
<213> ORGANISM: Bacteriophage T7

<400> SEQUENCE: 61

Ala Ala Gly Ala Val Val Phe Gln
1               5

<210> SEQ ID NO 62
<211> LENGTH: 10
<212> TYPE: PRT
<213> ORGANISM: Bacteriophage T7

<400> SEQUENCE: 62

Ala Ala Gly Ala Val Val Phe Lys Val Glu
1               5                   10

<210> SEQ ID NO 63
<211> LENGTH: 9
<212> TYPE: PRT
<213> ORGANISM: Bacteriophage T7

<400> SEQUENCE: 63

Ala Ala Gly Ala Val Val Phe Gln Ser
1               5

<210> SEQ ID NO 64
<211> LENGTH: 10
<212> TYPE: PRT
<213> ORGANISM: Bacteriophage T7

<400> SEQUENCE: 64

Ala Ala Gly Ala Val Val Phe Ser Gln Val
1               5                   10
```

```
<210> SEQ ID NO 65
<211> LENGTH: 10
<212> TYPE: PRT
<213> ORGANISM: Bacteriophage T7

<400> SEQUENCE: 65

Ala Ala Gly Ala Val Val Phe Gln Ser Glu
1               5                   10

<210> SEQ ID NO 66
<211> LENGTH: 13
<212> TYPE: PRT
<213> ORGANISM: Bacteriophage T7

<400> SEQUENCE: 66

Ala Ala Gly Ala Val Val Phe Gln Ser Gly Ala Ala Arg
1               5                   10

<210> SEQ ID NO 67
<211> LENGTH: 9
<212> TYPE: PRT
<213> ORGANISM: Bacteriophage T7

<400> SEQUENCE: 67

Leu Gly Asp Pro Asn Ser Asp Gly Ala
1               5

<210> SEQ ID NO 68
<211> LENGTH: 4
<212> TYPE: PRT
<213> ORGANISM: Bacteriophage T7

<400> SEQUENCE: 68

Asp Gly Ala Ile
1

<210> SEQ ID NO 69
<211> LENGTH: 4
<212> TYPE: PRT
<213> ORGANISM: Bacteriophage T7

<400> SEQUENCE: 69

Asp Gly Ala Ala
1

<210> SEQ ID NO 70
<211> LENGTH: 6
<212> TYPE: PRT
<213> ORGANISM: Bacteriophage T7

<400> SEQUENCE: 70

Asp Gly Ala Leu Ala Ser
1               5

<210> SEQ ID NO 71
<211> LENGTH: 6
<212> TYPE: PRT
<213> ORGANISM: Bacteriophage T7

<400> SEQUENCE: 71

Asp Gly Ala Leu Ser Ser
1               5
```

-continued

<210> SEQ ID NO 72
<211> LENGTH: 5
<212> TYPE: PRT
<213> ORGANISM: Bacteriophage T7

<400> SEQUENCE: 72

Asp Gly Ala Asp Leu
1               5

<210> SEQ ID NO 73
<211> LENGTH: 5
<212> TYPE: PRT
<213> ORGANISM: Bacteriophage T7

<400> SEQUENCE: 73

Asp Gly Ala Asn Leu
1               5

<210> SEQ ID NO 74
<211> LENGTH: 6
<212> TYPE: PRT
<213> ORGANISM: Bacteriophage T7

<400> SEQUENCE: 74

Asp Gly Ala Gly Val Tyr
1               5

<210> SEQ ID NO 75
<211> LENGTH: 6
<212> TYPE: PRT
<213> ORGANISM: Bacteriophage T7

<400> SEQUENCE: 75

Asp Gly Ala Leu Val Tyr
1               5

<210> SEQ ID NO 76
<211> LENGTH: 7
<212> TYPE: PRT
<213> ORGANISM: Bacteriophage T7

<400> SEQUENCE: 76

Asp Gly Ala Lys Ile Pro Tyr
1               5

<210> SEQ ID NO 77
<211> LENGTH: 20
<212> TYPE: PRT
<213> ORGANISM: Bacteriophage T7

<400> SEQUENCE: 77

Asp Gly Ala Val Ala Tyr Pro Pro Met Leu Pro Val Leu His Gly Ser
1               5                   10                  15

Leu Ala Arg Leu
        20

<210> SEQ ID NO 78
<211> LENGTH: 11
<212> TYPE: PRT
<213> ORGANISM: Bacteriophage T7

<400> SEQUENCE: 78

Asp Gly Ala Tyr Asn Ala Lys Thr Asp Arg Gly
1               5                   10

<210> SEQ ID NO 79
<211> LENGTH: 6
<212> TYPE: PRT
<213> ORGANISM: Bacteriophage T7

<400> SEQUENCE: 79

Asp Gly Ala Leu Val Tyr
1               5

<210> SEQ ID NO 80
<211> LENGTH: 7
<212> TYPE: PRT
<213> ORGANISM: Bacteriophage T7

<400> SEQUENCE: 80

Asp Gly Ala His Ser Ser Ser
1               5

<210> SEQ ID NO 81
<211> LENGTH: 8
<212> TYPE: PRT
<213> ORGANISM: Bacteriophage T7

<400> SEQUENCE: 81

Asp Gly Ala Ser Asn Leu Ser Ser
1               5

<210> SEQ ID NO 82
<211> LENGTH: 10
<212> TYPE: PRT
<213> ORGANISM: Bacteriophage T7

<400> SEQUENCE: 82

Asp Gly Ala Ala Arg Asn Thr Leu Ser Ser
1               5                  10

<210> SEQ ID NO 83
<211> LENGTH: 15
<212> TYPE: PRT
<213> ORGANISM: Bacteriophage T7

<400> SEQUENCE: 83

Asp Gly Ala Ala Ile Ser Ser Asp Gly Phe Ile Asn Gln Ser Ser
1               5                  10                  15

<210> SEQ ID NO 84
<211> LENGTH: 6
<212> TYPE: PRT
<213> ORGANISM: Bacteriophage T7

<400> SEQUENCE: 84

Asp Gly Ala Leu Ser Ser
1               5

<210> SEQ ID NO 85
<211> LENGTH: 6
<212> TYPE: PRT
<213> ORGANISM: Bacteriophage T7

<400> SEQUENCE: 85

Asp Gly Ala Leu Ala Ser
1               5

-continued

```
<210> SEQ ID NO 86
<211> LENGTH: 5
<212> TYPE: PRT
<213> ORGANISM: Bacteriophage T7

<400> SEQUENCE: 86

Asp Gly Ala Trp Ser
1               5

<210> SEQ ID NO 87
<211> LENGTH: 6
<212> TYPE: PRT
<213> ORGANISM: Bacteriophage T7

<400> SEQUENCE: 87

Asp Gly Ala Asn Ser Pro
1               5

<210> SEQ ID NO 88
<211> LENGTH: 6
<212> TYPE: PRT
<213> ORGANISM: Bacteriophage T7

<400> SEQUENCE: 88

Asp Gly Ala Ser Ser Val
1               5

<210> SEQ ID NO 89
<211> LENGTH: 13
<212> TYPE: PRT
<213> ORGANISM: Bacteriophage T7

<400> SEQUENCE: 89

Asp Gly Ala Ser Asp Arg Gly Asn Glu Glu Met Ser Phe
1               5                   10

<210> SEQ ID NO 90
<211> LENGTH: 7
<212> TYPE: PRT
<213> ORGANISM: Bacteriophage T7

<400> SEQUENCE: 90

Asp Gly Ala Met Ser Pro Leu
1               5

<210> SEQ ID NO 91
<211> LENGTH: 13
<212> TYPE: PRT
<213> ORGANISM: Bacteriophage T7

<400> SEQUENCE: 91

Asp Gly Ala Val Pro Ser Val Ser Ser Pro Ser Ile Gly
1               5                   10

<210> SEQ ID NO 92
<211> LENGTH: 9
<212> TYPE: PRT
<213> ORGANISM: Bacteriophage T7

<400> SEQUENCE: 92

Asp Gly Ala Ser Gly Pro Ser Val Gly
1               5
```

```
<210> SEQ ID NO 93
<211> LENGTH: 8
<212> TYPE: PRT
<213> ORGANISM: Bacteriophage T7

<400> SEQUENCE: 93

Asp Gly Ala Thr Thr Ser Leu Gly
1               5

<210> SEQ ID NO 94
<211> LENGTH: 5
<212> TYPE: PRT
<213> ORGANISM: Bacteriophage T7

<400> SEQUENCE: 94

Asp Gly Ser Gln Met
1               5

<210> SEQ ID NO 95
<211> LENGTH: 10
<212> TYPE: PRT
<213> ORGANISM: Bacteriophage T7

<400> SEQUENCE: 95

Asp Gly Ala Pro Ser Leu Ser Val Gly Gly
1               5                   10

<210> SEQ ID NO 96
<211> LENGTH: 9
<212> TYPE: PRT
<213> ORGANISM: Bacteriophage T7

<400> SEQUENCE: 96

Asp Gly Ala Thr Thr Val Asp Asn Met
1               5

<210> SEQ ID NO 97
<211> LENGTH: 12
<212> TYPE: PRT
<213> ORGANISM: Bacteriophage T7

<400> SEQUENCE: 97

Asp Gly Ala Asn Leu Val Ser Gly Thr Arg Leu Asp
1               5                   10

<210> SEQ ID NO 98
<211> LENGTH: 5
<212> TYPE: PRT
<213> ORGANISM: Bacteriophage T7

<400> SEQUENCE: 98

Asp Gly Ala Thr Gly
1               5

<210> SEQ ID NO 99
<211> LENGTH: 9
<212> TYPE: PRT
<213> ORGANISM: Bacteriophage T7

<400> SEQUENCE: 99

Asp Gly Ala Thr Thr Gln Thr Ala Tyr
1               5
```

```
<210> SEQ ID NO 100
<211> LENGTH: 8
<212> TYPE: PRT
<213> ORGANISM: Bacteriophage T7

<400> SEQUENCE: 100

Asp Gly Ala Ser Asn Leu Pro Leu
1               5

<210> SEQ ID NO 101
<211> LENGTH: 8
<212> TYPE: PRT
<213> ORGANISM: Bacteriophage T7

<400> SEQUENCE: 101

Asp Gly Ala Ala Thr Arg Gly Arg
1               5

<210> SEQ ID NO 102
<211> LENGTH: 14
<212> TYPE: PRT
<213> ORGANISM: Bacteriophage T7

<400> SEQUENCE: 102

Asp Gly Ala Ser Lys Lys Thr Val Leu Ala Met Asn Pro Arg
1               5                   10

<210> SEQ ID NO 103
<211> LENGTH: 10
<212> TYPE: PRT
<213> ORGANISM: Bacteriophage T7

<400> SEQUENCE: 103

Asp Gly Ala Thr His Gly Ser Glu Val Ala
1               5                   10

<210> SEQ ID NO 104
<211> LENGTH: 6
<212> TYPE: PRT
<213> ORGANISM: Bacteriophage T7

<400> SEQUENCE: 104

Asp Gly Ala Val Pro Leu
1               5

<210> SEQ ID NO 105
<211> LENGTH: 5
<212> TYPE: PRT
<213> ORGANISM: Bacteriophage T7

<400> SEQUENCE: 105

Asp Gly Ala Arg Ala
1               5

<210> SEQ ID NO 106
<211> LENGTH: 6
<212> TYPE: PRT
<213> ORGANISM: Bacteriophage T7

<400> SEQUENCE: 106

Asp Gly Ala Met Val Gly
1               5
```

```
<210> SEQ ID NO 107
<211> LENGTH: 7
<212> TYPE: PRT
<213> ORGANISM: Bacteriophage T7

<400> SEQUENCE: 107

Asp Gly Ala Val Arg Arg Gly
1               5

<210> SEQ ID NO 108
<211> LENGTH: 7
<212> TYPE: PRT
<213> ORGANISM: Bacteriophage T7

<400> SEQUENCE: 108

Asp Gly Ala Ala Leu Val Leu
1               5

<210> SEQ ID NO 109
<211> LENGTH: 7
<212> TYPE: PRT
<213> ORGANISM: Bacteriophage T7

<400> SEQUENCE: 109

Asp Gly Ala Met Ser Pro Leu
1               5

<210> SEQ ID NO 110
<211> LENGTH: 8
<212> TYPE: PRT
<213> ORGANISM: Bacteriophage T7

<400> SEQUENCE: 110

Asp Gly Ala Ser Asn Leu Pro Leu
1               5

<210> SEQ ID NO 111
<211> LENGTH: 7
<212> TYPE: PRT
<213> ORGANISM: Bacteriophage T7

<400> SEQUENCE: 111

Asp Gly Ala Ala Leu Val Leu
1               5

<210> SEQ ID NO 112
<211> LENGTH: 8
<212> TYPE: PRT
<213> ORGANISM: Bacteriophage T7

<400> SEQUENCE: 112

Asp Gly Ala Ala Thr Arg Gly Arg
1               5

<210> SEQ ID NO 113
<211> LENGTH: 7
<212> TYPE: PRT
<213> ORGANISM: Bacteriophage T7

<400> SEQUENCE: 113

Asp Gly Ala Val Arg Arg Gly
1               5
```

```
<210> SEQ ID NO 114
<211> LENGTH: 9
<212> TYPE: PRT
<213> ORGANISM: Bacteriophage T7

<400> SEQUENCE: 114

Asp Gly Ala Thr Thr Val Asp Asn Met
1               5

<210> SEQ ID NO 115
<211> LENGTH: 9
<212> TYPE: PRT
<213> ORGANISM: Bacteriophage T7

<400> SEQUENCE: 115

Asp Gly Ala Thr Thr Gln Thr Ala Tyr
1               5

<210> SEQ ID NO 116
<211> LENGTH: 14
<212> TYPE: PRT
<213> ORGANISM: Bacteriophage T7

<400> SEQUENCE: 116

Asp Gly Ala Ser Lys Lys Thr Val Leu Ala Met Asn Pro Arg
1               5                   10

<210> SEQ ID NO 117
<211> LENGTH: 8
<212> TYPE: PRT
<213> ORGANISM: Bacteriophage T7

<400> SEQUENCE: 117

Asp Gly Ala Thr Thr Ser Leu Gly
1               5

<210> SEQ ID NO 118
<211> LENGTH: 5
<212> TYPE: PRT
<213> ORGANISM: Bacteriophage T7

<400> SEQUENCE: 118

Asp Gly Ser Gln Met
1               5

<210> SEQ ID NO 119
<211> LENGTH: 4
<212> TYPE: PRT
<213> ORGANISM: Bacteriophage T7

<400> SEQUENCE: 119

Phe Ser Gln Val
1

<210> SEQ ID NO 120
<211> LENGTH: 11
<212> TYPE: PRT
<213> ORGANISM: Bacteriophage T7

<400> SEQUENCE: 120

Phe Gln Ser Gly Val Met Leu Gly Asp Pro Asn
1               5                   10
```

```
<210> SEQ ID NO 121
<211> LENGTH: 11
<212> TYPE: PRT
<213> ORGANISM: Bacteriophage T7

<400> SEQUENCE: 121

Ser Ser Val Asp Lys Leu Ala Ala Ala Leu Glu
1               5                   10

<210> SEQ ID NO 122
<211> LENGTH: 10
<212> TYPE: PRT
<213> ORGANISM: Bacteriophage T7

<400> SEQUENCE: 122

Gly Ala Val Lys Leu Ala Ala Ala Leu Glu
1               5                   10

<210> SEQ ID NO 123
<211> LENGTH: 16
<212> TYPE: DNA
<213> ORGANISM: OLIGO

<400> SEQUENCE: 123
gaattcggac ggtgcc                                                       16

<210> SEQ ID NO 124
<211> LENGTH: 15
<212> TYPE: DNA
<213> ORGANISM: OLIGO

<400> SEQUENCE: 124
ggggctggaa agctt                                                        15

<210> SEQ ID NO 125
<211> LENGTH: 15
<212> TYPE: DNA
<213> ORGANISM: OLIGO

<400> SEQUENCE: 125
aagctttcca gcccc                                                        15
```

IN VITRO PROCESS FOR SELECTING PHAGE RESISTANT TO BLOOD INACTIVATION

This application is related to prior provisional application Nos. 60/131,151 filed on Apr. 27, 1999 and 60/139,431 filed on Jun. 7, 1999.

FEDERALLY SPONSORED RESEARCH

This invention was made under a contract with an agency of the United States Government: U.S. Government agency: NIH Government contract number: 5 R21 DK53314-02

FIELD OF THE INVENTION

The present invention relates to compositions and methods for the selection and use of surface exposed epitopes. The present invention includes in vivo and in vitro phage peptide display methods for the identification and selection of peptides and peptide associated factors with desired properties (e.g., targeting specificity, stability, etc.). The present invention further provides methods and compositions for the isolation and identification of peptide-specific antibodies and includes methods and compositions employing nuclear localization signals for enhanced nuclear transport and expression of DNA.

BACKGROUND

Drug Delivery

A variety of methods and routes of administration have been developed to deliver pharmaceuticals that include small molecular drugs and biologically-active compounds such as peptides, hormones, proteins, and enzymes to their site of action. Parenteral routes of administration include intravascular (intravenous, intraarterial), intramuscular, intraparenchymal, intradermal, subdermal, subcutaneous, intratumor, intraperitoneal and intralymphatic injections that use a syringe and a needle or catheter. The blood circulatory system provides systemic spread of the pharmaceutical. Polyethylene glycol and other hydrophilic polymers have provided protection of the pharmaceuticals in the blood stream by preventing their interaction with blood components and increasing the circulatory time of the pharmaceuticals through preventing opsonization, phagocytosis and uptake by the reticuloendothelial system. For example, the enzyme adenosine deaminase has been covalently modified with polyethylene glycol to increase the circulatory time and persistence of this enzyme in the treatment of patients with adenosine deaminase deficiency.

The controlled release of pharmaceuticals after their administration is under intensive development. Pharmaceuticals have also been complexed with a variety of biologically-labile polymers to delay their release from depots. These polymers have included copolymers of poly (lactic/glycolic acid) (PLGA) (Jain, R. et al. Drug Dev. Ind. Pharm. 24, 703–727 (1998), ethylvinyl acetate/polyvinyl alcohol (Metrikin, DC and Anand, R, Curr Opin Ophthalmol 5, 21–29, 1994) as typical examples of biodegradable and non-degradable sustained release systems respectively.

Transdermal routes of administration have been effected by patches and ionotophoresis. Other epithelial routes include oral, nasal, respiratory, and vaginal routes of administration. These routes have attracted particular interest for the delivery of peptides, proteins, hormones, and cytokines which are typically administered by parenteral routes using needles. For example, the delivery of insulin via respiratory, oral, or nasal routes would be very attractive for patients with diabetes mellitus. For oral routes, the acidity of the stomach (pH less than 2) is avoided for pH-sensitive compounds by concealing peptidase-sensitive polypeptides inside pH-sensitive hydrogel matrix (copolymers of polyethyleneglycol and polyacrylic acid). After passing low pH compartments of gastrointestinal tract such structures swell at higher pH releasing thus a bioactive compound (Lowman AM et al. J. Pharm. Sci. 88, 933–937 (1999). Capsules have also been developed that release their contents within the small intestine based upon pH-dependent solubility of a polymer. Copolymers of polymethacrylic acid (Eudragit S, Rohm America) are known as polymers which are insoluble at lower pH but readily solubilized at higher pH, so they are used as enteric coatings (Z Hu et al. J. Drug Target., 7, 223, 1999).

Biologically active molecules may be assisted by a reversible formation of covalent bonds. Quite often, it is found that the drug administered to a patient is not the active form of the drug, but what is a called a prodrug that changes into the actual biologically active compound upon interactions with specific enzymes inside the body. In particular, anticancer drugs are quite toxic and are administered as prodrugs which do not become active until they come in contact with the cancerous cells (Sezaki, II., Takakura, Y., Hashida, M. *Adv. Drug. Delivery Reviews* 3, 193, 1989).

Liposomes were also used as drug delivery vehicles for low molecular weight drugs and macromolecules such as amphotericin B for systemic fungal infections and candidiasis. Inclusion of anti-cancer drugs such as adriamycin has been developed to increase their delivery to tumors and reducetheir access to other tissue sites (e.g. heart) thereby decreasing their toxicity. The use of pH-sensitive polymers in conjunction with liposomes represents another opportunity to modulate lipid bilayer permeability warranting thus triggered release of encapsulated drugs. For example, hydrophobically-modified N-isopropylacrylamide-methacrylic acid copolymer can render regular egg PC liposomes pH-sensitive by pH-dependent interaction of grafted aliphatic chains with lipid bilayer (O Meyer et al., FEBS Lett., 421, 61, 1998).

Gene And Nucleic Acid-Based Delivery

Gene or polynucleotide transfer is the cardinal process of gene therapy. The gene needs to be transferred across the cell membrane and enter the nucleus where the gene can be expressed. Gene transfer methods currently being explored include viral vectors and physical-chemical methods.

Viruses have evolved over millions of years to transfer their genes into mammalian cells. Viruses can be modified to carry a desired gene and become a "vector" for gene therapy. Using standard recombinant techniques, the harmful or superfluous viral genes can be removed and replaced with the desired normal genes. This was first accomplished with mouse retroviruses. The development of retroviral vectors were the catalyst that promoted current gene therapy efforts. However, they cannot infect all cell types very efficiently, especially in vivo. Other viral vectors based on Herpes virus are being developed to enable more efficient gene transfer into brain cells. Adenoviral and adenoassociated vectors are being developed to infect lung and other types of cells.

Besides using viral vectors, it is possible to directly transfer genes into mammalian cells. Usually, the desired gene is placed within bacterial plasmid DNA along with a mammalian promoter, enhancer, and other sequences that enable the gene to be expressed in mammalian cells. Several milligrams of the plasmid DNA containing all these sequences can be prepared and purified from the bacterial cultures. The plasmid DNA containing the desired gene can be incorporated into lipid vesicles (liposomes including cationic lipids such as Lipofectin) that then transfer the plasmid DNA into the target cell. Plasmid DNA can also be complexed with proteins that target the plasmid DNA to specific tissues, just as certain proteins are taken up (endocytosed) by specific cells. Also, plasmid DNA can be complexed with polymers such as polylysine and polyethylenimine. Another plasmid-based technique involves "shooting" the plasmid DNA on small gold beads into the cell using a "gun". Finally, muscle cells in vivo have the unusual ability to take up and express plasmid DNA Gene therapy approaches can be classified into direct and indirect methods. Some of these gene transfer methods are most effective when directly injected into a tissue space. Direct methods using many of the above gene transfer techniques are being used to target tumors, muscle, liver, lung, and brain. Other methods are most effective when applied to cells or tissues that have been removed from the body, genetically modified and then transplanted back into the body. Indirect approaches in conjunction with retroviral vectors are being developed to transfer genes into bone marrow cells, lymphocytes, hepatocytes, myoblasts and skin cells.

Gene Therapy And Nucleic Acid-Based Therapies

Gene therapy is a revolutionary advance in the treatment of disease. It is an approach for treating disease which is different from the conventional surgical and pharmaceutical therapies. Conceptually, gene therapy is a relatively simple approach. If someone has a defective gene, then gene therapy would fix the defective gene. The disease state would be modified by manipulating genes instead of the gene products. Although, the initial motivation for gene therapy was the treatment of genetic disorders, it is becoming increasingly apparent that gene therapy will be useful for the treatment of a broad range of acquired diseases such as cancer, infectious disorders (AIDS), heart disease, arthritis, and neurodegenerative disorders (Parkinsons and Alzheimers).

Gene therapy promises to take full-advantage of the major advances brought about by molecular biology. While biochemistry is mainly concerned with how the cell obtains the energy and matter that is required for normal function, molecular biology is mainly concerned with how the cell gets the information to perform its functions. Molecular biology wants to discover the flow of information in the cell. Using the metaphor of computers, the cell is the hardware while the genes are the software. In this sense, the purpose of gene therapy is to provide the cell with a new program (genetic information) so as to reprogram a dysfunctional cell to perform a normal function. The addition of a new cellular function is provided by the insertion of a foreign gene that expresses a foreign protein or a native protein at amounts that are not initially present in the patient.

The inhibition of a cellular function is provided by anti-sense approaches (that is acting against messenger RNA) and that includes using oligonucleotides complementary to the messenger RNA sequence and ribozymes. Messenger RNA (mRNA) is an intermediate in the expression of the DNA gene. The mRNA is translated into a protein. "Anti-sense" methods use a RNA sequence or an oligonucleotide that is made complementary to the target mRNA sequence and therefore binds specifically to the target messenger RNA. When this anti-sense sequence binds to the target mRNA, the mRNA is somehow destroyed or blocked from being translated. Ribozymes destroy a specific mRNA by a different mechanism. Ribozymes are RNA's that contain sequence complementary to the target messenger RNA plus a RNA sequence that acts as an enzyme to cleave the messenger RNA, thus destroying it and preventing it from being translated. When these anti-sense or ribozyme sequences are introduced into a cell, they would inactivate their specific target mRNA and reduce their disease-causing properties.

Several recessive genetic disorders are being considered for gene therapy. One of the first uses of gene therapy in humans has been used for the genetic deficiency of the adenosine deaminase (ADA) gene. Other clinical gene therapy trials have been conducted for cystic fibrosis, familial hypercholesteremia caused by a defective LDL-receptor gene and partial ornithine transcarbomylase deficiency. Both indirect and direct gene therapy approaches are being developed for Duchenne muscular dystrophy. Patients with this type of muscular dystrophy eventually die from loss of their respiratory muscles. Direct approaches include the intramuscular injection of naked plasmid DNA or adenoviral vectors.

A wide variety of gene therapy approaches for cancer are under investigation in animals and in human clinical trials. One approach is to express in lymphocytes and in the tumor cells cytokine genes that stimulate the immune system to destroy the cancer cells. The cytokine genes would be transferred into the lymphocytes by removing the lymphocytes from the body and infecting them with a retroviral vector carrying the cytokine gene. The tumor cells would be similarly genetically modified by this indirect approach to express cytokines within the tumor. Direct approaches involving the expression of cytokines in tumor cells in situ are also being considered. Other genes besides cytokines may be able to induce an immune response against the cancer. One approach that has entered clinical trials is the direct injection of HLA-B7 gene (which encodes a potent immunogen) within lipid vesicles into malignant melanomas in order to induce a more effective immune response against the cancer.

"Suicide" genes are genes that kill cells which express the gene. For example, the diphtheria toxin gene directly kill cells. The Herpes thymidine kinase (TK) gene kills cells in conjunction with acyclovir (a drug used to treat Herpes viral infections). Other gene therapy approaches take advantage of our knowledge of oncogenes and suppressor tumor genes-also known as anti-oncogenes. The loss of a functioning anti-oncogene plays a decisive role in childhood tumors such as retinoblastoma, osteosarcoma and Wilms tumor and may play an important role in more common tumors such as lung, colon and breast cancer. Introduction of the normal anti-oncogene back into these tumor cells may convert them back to normal cells. The activation of oncogenes also plays an important role in the development of cancers. Since these oncogenes operate in a "dominant" fashion, treatment will require inactivation of the abnormal oncogene. This can be done using either "anti-sense" or ribozyme methods that selectively inactivate a specific messenger RNA in a cell.

Gene therapy can be used as a type of vaccination to prevent infectious diseases and cancer. When a foreign gene is transferred into a cell and the protein is made, the foreign protein is presented to the immune system differently from simply injecting the foreign protein into the body. This different presentation is more likely to cause a cell-mediated immune response which is important for fighting latent viral infections such as human immunodeficiency virus (HIV causes AIDS), Herpes and cytomegalovirus. Expression of the viral gene within a cell simulates a viral infection and induces a more effective immune response by fooling the body that the cell is actually infected by the virus, without the danger of an actual viral infection.

One direct approach uses the direct intramuscular injection of naked plasmid DNA to express a viral gene in muscle cells. The "gun" has also been shown to be effective at inducing an immune response by expressing foreign genes in the skin. Other direct approaches involving the use of retroviral, vaccinia or adenoviral vectors are also being developed. An indirect approach has been developed to remove fibroblasts from the skin, infect them with a retroviral vector carrying a viral gene and transplant the cells back into the body. The envelope gene from the AIDS virus (HIV) is often used for these purposes. Many cancer cells express specific genes that normal cells do not. Therefore, these genes specifically expressed in cancer cells can be used for immunization against cancer.

Besides the above immunization approaches, several other gene therapies are being developed for treating infectious disease. Most of these new approaches are being developed for HIV infection and AIDS. Many of them will involve the delivery of anti-sense or ribozyme sequences directed against the particular viral messenger RNA. These anti-sense or ribozyme sequences will block the expression of specific viral genes and abort the viral infection without damaging the infected cell. Another approach somewhat similar to the ant-sense approaches is to overexpress the target sequences for these regulatory HIV sequences.

Gene therapy efforts would be directed at lowering the risk factors associated with atherosclerosis. Overexpression of the LDL receptor gene would lower blood cholesterol in patients not only with familial hypercholesteremia but with other causes of high cholesterol levels. The genes encoding the proteins for HDL ("the good cholesterol") could be expressed also in various tissues. This would raise HDL levels and prevent atherosclerosis and heart attacks. Tissue plasminogen activator (tPA) protein is being given to patients immediately after their myocardial infarction to digest the blood clots and open up the blocked coronary blood vessels. The gene for tPA could be expressed in the endothelial cells lining the coronary blood vessels and thereby deliver the tPA locally without providing tPA throughout the body. Another approach for coronary vessel disease is to express a gene in the heart that produces a protein that causes new blood vessels to grow. This would increase collateral blood flow and prevent a myocardial infarction from occurring.

Neurodegenerative disorders such as Parkinson's and Alzheimer's diseases are good candidates for early attempts at gene therapy. Arthritis could also be treated by gene therapy. Several proteins and their genes (such as the IL-1 receptor antagonist protein) have recently been discovered to be anti-inflammatory. Expression of these genes in joint (synovial) fluid would decrease the joint inflammation and treat the arthritis.

In addition, methods are being developed to directly modify the sequence of target genes and chromosomal DNA. The delivery of a nucleic acid or other compound that modifies the genetic instruction (e.g., by homologous recombination) can correct a mutated gene or mutate a functioning gene.

Liver Gene Therapy

Liver is one of the most important target tissues for gene therapy given its central role in metabolism (e.g. lipoprotein metabolism in various hypercholesterolemias) and the secretion of circulating proteins (e.g. clotting factors in hemophilia). At least one hundred different genetic disorders could be corrected by liver-directed gene therapy. Their cumulative frequency is approximately one percent of all births. In addition, multifactorial disorders are also amenable to liver gene therapy. For example, diabetes mellitus could be treated by expressing the insulin gene within hepatocytes whose physiology may enable glucoseregulated insulin secretion. Acquired disorders such as chronic hepatitis (particularly important in Asia) could also be treated by polynucleotide-based liver therapies.

A variety of techniques have been developed to transfer genes into the liver. Jon Wolff and colleagues suggested the liver as a target tissue for gene therapy by demonstrating that primary hepatocytes could be efficiently infected with retroviral vectors (Wolff, et al., Proc. Natl. Acad. Sci. USA, 84:3444–3348. 1987). Cultured hepatocytes have been genetically modified by retroviral vectors and implanted back into livers of animals and humans (Grossman, et al., Nature Genet., 6:335–341. 1994, Chowdhury, et al., Science, 254:1802–1805. 1991, Ledley, et al., Somat. Cell Mol. Genet., 13:145–54. 1987). Retroviral vectors have also been delivered directly to livers in which hepatocyte division was induced by partial hepatectomy or cytokines (Bosch, et al., Journal of Clinical Investigation, 98:2683–7. 1996, Ferry, et al., Proc. Natl. Acad. Sci. USA, 88:8377–8381. 1991, Kaleko, et al., Hum. Gene Ther., 2:27–32. 1991, Kay, et al., Hum. Gene Ther., 3:641–7. 1992, Hafenrichter, et al., J. Surgical Res., 56:510–7. 1994, Rettinger, et al., Proc. Natl. Acad. Sci. USA, 91:1460–4. 1994). Injection of adenoviral vectors into the portal or systemic circulatory systems leads to high levels of foreign gene expression that is transient (Sullivan, et al., Human Gene Therapy, 8:1195–206. 1997, Jaffe, et al., Nature Genet., 1:372–378. 1992, Li, et al., Hum. Gene Ther., 4:403–409. 1993, Stratford-Perricaudet, et al., Hum. Gene Ther., 1:241–56. 1990). Long-term expression of AAV vectors or retroviral vectors derived from *lentiviruses* has been recently reported for liver and muscle (Snyder, et al., Nature Genetics, 16:270–6. 1997, Herzog, et al., Nature Medicine, 5:56–63. 1999, Linden and Woo, Nature Medicine, 5:21–22. 1999, Snyder, et al., Nature Medicine, 5:64–70, 1999) (Xiao, et al., Journal of Virology, 70:8098–8108, 1996, Fisher, et al., Nature Medicine, 3:306–312. 1997, Herzog, et al., Proceedings of the National Academy of Sciences of the United States of America, 94:5804–5809. 1997) (Kafri, et al., Nature Genetics, 17:214–317. 1997). Since AAV and retroviral vectors require administration directly in the liver or its blood vessels, hepatocyte-targeting peptides would improve their utility. Adenoviral vectors can target hepatocytes after peripheral vein injection but hepatocyte targeting would improve their safety and efficacy. Several groups are developing approaches to modify the targeting of retroviral and adenoviral vectors, that could readily incorporate the peptides discovered in this proposal (Reynolds and Curiel, The Development of Human Gene Therapy. Editor: T. Friedmann, Cold Spring arbor Press, pp. 111–130. 1999).

Non-viral transfer methods have included polylysine complexes of asialoglycoproteins that are systemically administered (Wu and Wu, Biochemistry, 27:887–92. 1988, Wu, et al., Journal of Biological Chemistry, 264:16985–7. 1989, Wilson, et al., Journal of Biological Chemistry, 267:963–7. 1992). Plasmid DNA expression in the liver has also been achieved via liposomes delivered by tail vein or intraportal routes (Kaneda, et al., J. Biol. Chem., 264:12126–12129. 1989, Kaneda, et al., Science, 243:375–378. 1989, Soriano, et al., Proc. Natl. Acad. Sci. USA, 80:7128–7131. 1993). One lab has shown that high levels of hepatocyte expression can be achieved by the injection of naked plasmid DNA (pDNA) into liver vessels or tail vein (Budker, et al., Gene Therapy, 3:593–8. 1996, Zhang, et al., Human Gene Therapy, 8:1763–72. 1997).

Paradigm For Development of Vectors

The current paradigm for the development of non-viral and viral vectors is to incorporate in a combinatorial fashion functional groups that enable particular transfer steps. These functional groups, initially discovered within proteins and viruses, serve as signals or "addresses" that interact with cellular components and cause the protein or virus to enter a particular sub-cellular compartment. These same signals can be incorporated into non-viral or viral vectors to enhance each transport step required for the therapeutic genes to eventually enter the cellular nucleus where the gene expresses its therapeutic function. These signals include surface molecules that resist inactivation in the blood, maintaining their ability to direct the vector toward target cells. After particle binding to the cell, the particle must contain other molecules to release the particle DNA into the cytoplasm. Finally, other functional groups can enable cytoplasmic transport to the nuclear membrane and traversal of the nuclear pore into the nucleus.

Polymers for Drug and Nucleic Acid Delivery

Polymers are used for drug delivery for a variety of therapeutic purposes. Polymers have also been used in research for the delivery of nucleic acids (polynucleotides and oligonucleotides) to cells with an eventual goal of providing therapeutic processes. Such processes have been termed gene therapy or anti-sense therapy. One of the several methods of nucleic acid delivery to the cells is the use of DNA-polycation complexes. It has been shown that cationic proteins like histones and protamines or synthetic polymers like polylysine, polyarginine, polyornithine, DEAE dextran, polybrene, and polyethylenimine may be effective intracellular delivery agents while small polycations like spermine are ineffective. The following are some important principles involving the mechanism by which polycations facilitate uptake of DNA.

Polycations provide attachment of DNA to the cell surface. The polymer forms a cross-bridge between the polyanionic nucleic acids and the polyanionic surfaces of the cells. As a result the main mechanism of DNA translocation to the intracellular space might be non-specific adsorptive endocytosis which may be more effective then liquid endocytosis or receptor-mediated endocytosis. Furthermore, polycations are a convenient linker for attaching specific receptors to DNA and as result, DNA- polycation complexes can be targeted to specific cell types.

Polycations protect DNA in complexes against nuclease degradation. This is important for both extra- and intracellular preservation of DNA. Gene expression is also enabled or increased by preventing endosome acidification with $NH_4Cl$ or chloroquine. Polyethylenimine, which facilitates gene expression without additional treatments, probably disrupts endosomal function itself. Disruption of endosomal function has also been accomplished by linking to the polycation endosomal-disruptive agents such as fusion peptides or adenoviruses.

Polycations can also facilitate DNA condensation. The volume which one DNA molecule occupies in a complex with polycations is drastically lower than the volume of a free DNA molecule. The size of a DNA/polymer complex is probably critical for gene delivery in vivo. In terms of intravenous injection, DNA needs to cross the endothelial barrier and reach the parenchymal cells of interest. The largest endothelia fenestrae (holes in the endothelial barrier) occur in the liver and have an average diameter of 100 nm. The trans-epithelial pores in other organs are much smaller, for example, muscle endothelium can be described as a structure which has a large number of small pores with a radius of 4 nm, and a very low number of large pores with a radius of 20–30 nm. The size of the DNA complexes is also important for the cellular uptake process. After binding to the cells the DNA- polycation complex should be taken up by endocytosis. Since the endocytic vesicles have a homogenous internal diameter of about 100 nm in hepatocytes and are of similar size in other cell types, DNA complexes smaller than 100 nm are preferred.

Condensation of DNA

A significant number of multivalent cations with widely different molecular structures have been shown to induce condensation of DNA.

Two approaches for compacting (used herein as an equivalent to the term condensing) DNA:

1. Multivalent cations with a charge of three or higher have been shown to condense DNA. These include spermidine, spermine, $Co(NH_3)_6^{3+}$, $Fe^{3+}$, and natural or synthetic polymers such as histone H1, protamine, polylysine, and polyethylenimine. Analysis has shown DNA condensation to be favored when 90% or more of the charges along the sugar-phosphate backbone are neutralized.

2. Polymers (neutral or anionic) which can increase repulsion between DNA and its surroundings have been shown to compact DNA. Most significantly, spontaneous DNA self-assembly and aggregation process have been shown to result from the confinement of large amounts of DNA, due to excluded volume effect.

Depending upon the concentration of DNA, condensation leads to three main types of structures:

1) In extremely dilute solution (about 1 ug/mL or below), long DNA molecules can undergo a monomolecular collapse and form structures described as toroid.
2) In very dilute solution (about 10 ug/mL) microaggregates form with short or long molecules and remain in suspension. Toroids, rods and small aggregates can be seen in such solution.
3) In dilute solution (about 1 mg/mL) large aggregates are formed that sediment readily.

Toroids have been considered an attractive form for gene delivery because they have the smallest size. While the size of DNA toroids produced within single preparations has been shown to vary considerably, toroid size is unaffected by the length of DNA being condensed. DNA molecules from 400 bp to genomic length produce toroids similar in size. Therefore one toroid can include from one to several DNA molecules. The kinetics of DNA collapse by polycations that resulted in toroids is very slow. For example DNA condensation by $Co(NH_3)_6Cl_3$ needs 2 hours at room temperature.

The mechanism of DNA condensation is not clear. The electrostatic force between unperturbed helices arises primarily from a counterion fluctuation mechanism requiring multivalent cations and plays a major role in DNA condensation. The hydration forces predominate over electrostatic forces when the DNA helices approach closer then a few water diameters. In a case of DNA-polymeric polycation interactions, DNA condensation is a more complicated process than the case of low molecular weight polycations. Different polycationic proteins can generate toroid and rod formation with different size DNA at a ratio of positive to negative charge of 0.4. T4 DNA complexes with polyarginine or histone can form two types of structures; an elongated structure with a long axis length of about 350 nm (like free DNA) and dense spherical particles. Both forms exist simultaneously in the same solution. The reason for the coexistence of the two forms can be explained as an uneven distribution of the polycation chains among the DNA molecules. The uneven distribution generates two thermodynamically favorable conformations.

The electrophoretic mobility of DNA-polycation complexes can change from negative to positive in excess of polycation. It is likely that large polycations don't completely align along DNA but form polymer loops that interact with other DNA molecules. The rapid aggregation and strong intermolecular forces between different DNA molecules may prevent the slow adjustment between helices needed to form tightly packed orderly particles.

Preparation of polycation-condensed DNA particles is of particular importance for gene therapy, more specifically, particle delivery such as the design of non-viral gene transfer vectors. Optimal transfection activity in vitro and in vivo can require an excess of polycation molecules. However, the presence of a large excess of polycations may be toxic to cells and tissues. Moreover, the non-specific binding of cationic particles to all cells forestalls cellular targeting. Positive charge also has an adverse influence on biodistribution of the complexes in vivo.

Several modifications of DNA-cation particles have been created to circumvent the nonspecific interactions of the DNA-cation particle and the toxicity of cationic particles. Examples of these modifications include attachment of steric stabilizers, e.g. polyethylene glycol, which inhibit nonspecific interactions between the cation and biological polyanions. Another example is recharging the DNA particle by the additions of polyanions which interact with the cationic particle thereby lowering its surface charge, i.e. recharging of the DNA particle. We have demonstrated that layering of polyelectrolytes can be achieved on the surface of DNA/polycation particles (V S Trubetskoy, A Loomis, J E Hagstrom, V G Budker, J A Wolff. Nucleic Acids Res. 27:3090–3095, 1999, incorporated herein by reference). Another example is cross-linking the polymers and thereby caging the complex (V S Trubetskoy, A Loomis, P M Slattum, J E Hagstrom, V G Budker, J A Wolff. Bioconjugate Chem. 10:624–628, 1999, incorporated herein by reference). Nucleic acid particles can be formed by the formation of chemical bonds and template polymerization. Trubetskoy et al used two types of polymerization reactions to achieve DNA condensation: step polymerization and chain polymerization (V S Trubetskoy, V G Budker, L I Hanson, P M Slattum, J A Wolff, L E Hagstrom. Nucleic Acids Res. 26:4178–4185, 1998) U.S. patent application Ser. No. 08/778,657 incorporated herein by reference.

The Use of pH-Sensitive Lipids, Amphipathic Compounds, and Liposomes for Drug and Nucleic Acid Delivery After the landmark description of DOTMA (N-[1-(2,3-dioleyloxy)propyl]-N,N,N-trimethylammonium chloride) [Felgner, P L, Gadek, T R, Holm, M, et al. Lipofection: a highly efficient, lipid-mediated DNA-transfection procedure. Proc. Natl. Acad. Sci. USA. 1987;84:7413–7417], a plethora of cationic lipids have been synthesized. Basically, all the cationic lipids are amphipathic compounds that contain a hydrophobic domain, a spacer, and positively-charged amine. The hydrophilic domains are typically hydrocarbon chains such as fatty acids derived from oleic or myristic acid. The hydrocarbon chains are often joined either by ether or ester bonds to a spacer such as glycerol. Quaternary amines often compose the cationic groups. Usually, the cationic lipids are mixed with a fusogenic lipid such as DOPE (dioleoyl phosphatidyl ethanolamine) to form liposomes. The mixtures are mixed in chloroform that is then dried. Water is added to the dried lipid film and unilamellar liposomes form during sonication. Multilamellar cationic liposomes and cationic liposomes/DNA complexes prepared by the reverse-phase evaporation method have also been used for transfection. Cationic liposomes have also been prepared by an ethanol injection technique.

Several cationic lipids contain a spermine group for binding to DNA. DOSPA, the cationic lipid within the LipofectAMINE formulation (Life Technologies) contains a spermine linked via a amide bond and ethyl group to a trimethyl, quaternary amine [Hawley-Nelson, P, Ciccarone, V and Jessee, J. Lipofectamine reagent: A new, higher efficiency polycationic liposome transfection reagent. Focus 1993; 15:73–79]. A French group has synthesized a series of cationic lipids such as DOGS (dioctadecylglycinespermine) that contain spermine [Remy, J-S, Sirlin, C, Vierling, P, et al. Gene transfer with a series of lipophilic DNA-binding molecules. Bioconjugate Chem. 1994;5:647–654]. DNA has also been transfected by lipophilic polylysines which contain dipalmotoylsuccinylglycerol chemically-bonded to low molecular weight (~3000 MW) polylysine [Zhou, X Kilbanov, A and Huang, L. Lipophilic polylysines mediate efficient DNA transfection in mammalian cells. Biochim. Biophys. Acta 1991;1065:8–14. Zhou, X and Huang, L. DNA transfection mediated by cationic liposomes containing lipopolylysine: Characterization and mechanism of action Biochim. Biophys. Acta 1994;1195–203].

Other studies have used adjuvants with the cationic liposomes. Transfection efficiency into Cos cells was increased when amphiphilic peptides derived from influenza virus hemagglutinin were added to DOTMA/DOPE liposomes [Kamata, H, Yagisawa, H, Takahashi S, et al. Amphiphilic peptides enhance the efficiency of liposome-mediated DNA transfection. Nucleic Acids Res. 1994;22:536–537]. Cationic lipids have been combined with galactose ligands for targeting to the hepatocyte asialoglycoprotein receptor [Remy, J-S, Kichier, A, Mordvinov, V, et al. Targeted gene transfer into hepatoma cells with lipopolyamine-condensed DNA particles presenting galactose ligands: A stage toward artificial viruses. Proc. Nail. Acad. Sci. USA 1995;92:1744–1748]. Thiol-reactive phospholipids have also been incorporated into cationic lipid/pDNA complexes to enable cellular binding even when the net charge of the complex is not positive [Kichler, A, Remy, J-S, Boussif, O, et al. Efficient gene delivery with neutral complexes of lipospemmine and thiol-reactive phospholipids. Biochem. Biophys. Res. Comm. 1995;209:444–450]. DNA-dependent template process converted thiol-containing detergent possessing high critical micelle concentration into dimeric lipid-like molecule with apparently low water solubility (J P Behr and colleagues).

Cationic liposomes may deliver DNA either directly across the plasma membrane or via the endosome compartment. Regardless of its exact entry point, much of the DNA within cationic liposomes does accumulate in the endosome compartment. Several approaches have been investigated to prevent loss of the foreign DNA in the endosomal compartment by protecting it from hydrolytic digestion within the endosomes or enabling its escape from endosomes into the cytoplasm. They include the use of acidotropic (lysomotrophic), weak amines such as chloroquine that presumably prevent DNA degradation by inhibiting endosomal acidification [Legendre, J. & Szoka, F. Delivery of plasmid DNA into mammalian cell lines using pH-sensitive liposomes: Comparison with cationic liposomes. Pharmaceut. Res. 9, 1235–1242 (1992)]. Viral fusion peptides or whole virus have been included to disrupt endosomes or promote fusion of liposomes with endosomes, and facilitate release of DNA into the cytoplasm [Kamata, H., Yagisawa, H., Takahashi, S. & Hirata, H. Amphiphilic peptides enhance the efficiency of liposome-mediated DNA transfection. Nucleic Acids Res. 22, 536–537 (1994). Wagner, E., Curiel, D. & Cotten, M. Delivery of drugs, proteins and genes into cells using transferrin as a ligand for receptor-mediated endocytosis. *Advance Drug Delivery Reviews* 14, 113–135 (1994)].

Knowledge of lipid phases and membrane fusion has been used to design potentially more versatile liposomes that exploit the endosomal acidification to promote fusion with endosomal membranes. Such an approach is best exemplified by anionic, pH-sensitive liposomes that have been designed to destabilize or fuse with the endosome membrane at acidic pH [Duzgunes, N., Straubinger, R. M., Baldwin, P. A & Papahadjopoulos, D. *PH-sensitive liposomes*. (eds Wilschub, J. & Hoekstra, D.) p. 713–730 (Marcel Dekrer INC, 1991)]. All of the anionic, pH-sensitive liposomes have utilized phosphatidylethanolamine (PE) bilayers that are stabilized at non-acidic pH by the addition of lipids which contain a carboxylic acid group. Liposomes containing only PE are prone to the inverted hexagonal phase ($H_{II}$). In pH-sensitive, anionic liposomes, the carboxylic acid's negative charge increases the size of the lipid head group at pH greater than the carboxylic acid's pK and thereby stabilizes the phosphatidylethanolamine bilayer. At acidic pH within endosomes, the uncharged or reduced charge species is unable to stabilize the phosphatidylethanolamine-rich bilayer. Anionic, pH-sensitive liposomes have delivered a variety of membrane-impermeant compounds including DNA. However, the negative charge of these pH-sensitive liposomes prevents them from efficiently taking up DNA and interacting with cells; thus decreasing their utility for transfection. We have described the use of cationic, pH-sensitive liposomes to mediate the efficient transfer of DNA into a variety of cells in culture.

The Use of pH-Sensitive Polymers for Drug and Nucleic Acid Delivery pH-sensitive polymers have found broad application in the area of drug delivery exploiting various physiological and intracellular pH gradients for the purpose of controlled release of drugs (both low molecular weight and polymeric). pH sensitivity can be broadly defined as any change in polymer's physico-chemical properties over certain range of pH. More narrow definition demands significant changes in polymer's ability to retain (release) bioactive substance (drug) in physiologically tolerated pH range (usually pH 5.5–8). pH-sensitivity presumes the presence of ionizable groups in the polymer (polyion). All polyions can be divided into three categories based on their ability to donate or accept protons in aqueous solutions: polyacids, polybases and polyampholytes. Use of pH-sensitive polyacids in drug delivery applications usually relies on their ability to become soluble with the pH increase(acid/salt conversion), to form complex with other polymers over change of pH or undergo significant change in hydrophobicity/hydrophilicity balance. Combinations of all three above factors are also possible.

Copolymers of polymethacrylic acid (Eudragit S, Rohm America) are known as polymers which are insoluble at lower pH but readily solubilized at higher pH, so they are used as enteric coatings designed to dissolve at higher intestinal pH (Z Hu et al. J. Drug Target., 7, 223, 1999). Typical example of pH-dependent complexation is copolymers of polyacrylate(graft)ethyleneglycol which can be formulated into various pH-sensitive hydrogels which exhibit pH-dependent swelling and drug release (F Madsen et al., Biomaterials, 20, 1701, 1999). Hydrophobically-modified N-isopropylacrylamide-methacrylic acid copolymer can render regular egg PC liposomes pH-sensitive by pH-dependent interaction of grafted aliphatic chains with lipid bilayer (O Meyer et al., *FEBS Lett.*, 421, 61, 1998).

Polymers with pH-mediated hydrophobicity (like polyethylacrylic acid) can be used as endosomal disruptors for cytoplasmic drug delivery (N Murthy et al. J. Controlled Release 61, 137, 1999).

Polybases have found broad applications as agents for nucleic acid delivery in transfection/gene therapy applications due to the fact they are readily interact with polyacids. Typical example is polyethyleneimine (PEI). This polymer secures nucleic acid electrostatic adsorption on the cell surface followed by endocytosis of the whole complex. Cytoplasmic release of the nucleic acid occures presumably via so called "proton sponge" effect according to which pH-sensitivity of PEI is responsible for endosome rupture due to osmotic swelling during its acidification (O Boussif et al. Proc. Natl. Acad. Sci. USA 92, 7297, 1995). Cationic acrylates possess the similar activity (for example, poly-((2-dimethylamino)ethyl methacrylate) (P van de Wetering et al. J. Controlled Release 64, 193, 2000). However, polybases due to their polycationic nature pH-sensitive polybases have not find broad in vivo application so far. They exhibit acute systemic toxicity in vivo presumably mostly of colloid nature (JH Senior, Biochim. Biophys. Acta, 1070, 173, 1991). Milder polybases (for example, linear PEI) are better tolerated and can be used systemically for in vivo gene transfer (D Goula et al. Gene Therapy 5, 712, 1998).

Blood Interactions of Delivery Complexes

Blood interactions are of importance for in vivo delivery of drugs and genes. Retroviral vectors are inhibited in human blood through complement (C) activation(Russell, et al., Human Gene Therapy, 6:635–641. 1995, Welsh, et al., Nature, 257:612–614. 1975, Rother, et al., Hum. Gene Ther., 6:429–435. 1995). Retroviral vectors produced in non-human cell lines contain galactosyl($\alpha$1-3)galactosyl($\alpha$Gal) terminal sugars within glycolipids and glycoproteins (Cosset, et al., J. Virol., 69:7430–7436. 1995). Humans lack this sugar structure and produce antibodies against it (sensitized presumably by gut flora). Retroviral vectors produced in $\alpha$Gal-negative cell lines do not suffer this problem. Similar findings have been made for VSV, HIV-2, human foamy viruses and the vectors derived from them (Takeuchi, et al., J. Virol., 71:6174–6178. 1997). Another mechanism for retroviral inactivation involves C activation via direct binding of C1q to the p15 (envelope) transmembrane protein(Welsh, et al., Nature, 257:612–614. 1975, Pensiero, et al., Human Gene Therapy, 7:1095–1101. 1996, Bartholomew and Esser, Biochemistry, 19:2847–2853. 1980). Another viral vector system, baculovirus vectors (which can transduce mammalian hepatocytes), is inhibited by serum but not by C inactive serum (heat treated or depleted in C3 or C4)(Sandig, et al., Human Gene Therapy, 7:1937–1945. 1996). Other factors such as chondroitin sulfates within pleural effusions inhibit retroviral vector gene transfer(Batra, et al., J. Biol. Chem., 272:11736–11741. 1997).

Of relevance to the development of non-viral vectors, is the vast literature on the interactions of the C system and other serum factors with liposomes (Szebeni, Crit. Rev Therap. Drug Carrier Systems, 15:57–88. 1998). Opsonization of liposomes by serum proteins plays an important role in their clearance by the reticuloendothelial system (RES). For example, clearance of negatively-charged liposomes is aided by $\beta$2-glycoprotein I binding (Chonn, et al., J. Biol. Chem., 270:25845–25849. 1995). Generally, neutral liposomes are poor C activators but they are cleared similarly to anionic liposomes in vivo, possibly because they absorb anionic serum proteins in vivo (Devine and Bradley, Advanced Drug Delivery Reviews, 32:19–29. 1998).

"Plain" liposomes (phospholipid/cholesterol bilayers without antigenic components) bind several serum proteins including albumin, IgG, extracellular matrix proteins (fibronectin, laminin, serum amyloid protein), clotting factors, apolipoproteins, β2-glycoprotein-1, C reactive protein (CRP), α2-macroglobulin, and C factor such as C1q and C3 (Senior, Crit. Rev. Ther. Drug Carrier Syst., 3:123. 1987, Scherphof, et al., Liposome Technology, 205. 1984, Juliano, Liposomes, 53. 1983). Apo E binds to both anionic and neutral liposomes, but only the small, neutral liposomes had reduced liver targeting in apo E-deficient mice (Scherphof and Kamps, Advanced Drug Delivery Reviews, 32:81–97. 1998). This suggests that apo E-binding is important for the liver targeting of neutral but not anionic liposomes. Anionic liposomes activate C via the classical pathway starting with C1q (without anti-phosholipid antibodies), which leads to deposition of C3b and iC3b on the liposome's surface (Liu, et al., Biochim. Biophys. Acta, 1235:140–146. 1995) (Devine and Bradley, Advanced Drug Delivery Reviews, 32:19–29. 1998). Cationic liposomes activate C via the alternative pathway in human serum but weakly in rat serum. Another pathway is due to CRP binding of phosphocholine and galactosyl residues within liposomes (Volanakis and Narkates, J. Immunology, 126:1820–1825. 1981). The clearance of liposomes is affected by several other factors such as their size, fluidity, packing, and cholesterol content. In summary, the clearance of conventional liposomes is delayed by using small, neutral, unilamellar liposomes containing rigid bilayers (disteraroyl phosphatidylcholine or sphingomylein and cholesterol) (Lasic and Martin, Pharmacology and Toxicology: Basic and Clinical Aspects, 1995). Besides affecting delivery, C activation can also release anaphylatoxins (e.g., C3a, C4a, and C5a) that activate mast cells, basophils and platelets causing respiratory, blood pressure and dermatologic sequelae.

Many of this field's concepts and experimental methods are now being extended to the use of cationic lipids for DNA transfer. Serum inhibits the transfection ith the use of several types of cationic lipids by modifying the DNA/cationic lipid complexes (Escriou, et al., Biochim. Biophys. Acta, 1368:276–288. 1998, Zelphati and Szoka, Pharmaceutical Research, 13:1367–1372. 1996, Senior, et al., Biochimica et Biophysica Acta, 1070:173–9. 1991, Felgner, et al., Proc. Natl. Acad. Sci. USA, 84:7413–7417. 1987, Zelphati, et al., Biochim. Biophys. Acta, 1390:119–133. 1998, Li, et al., Gene Therapy, 5:930–937. 1998) (Yang and Huang, Gene Therapy, 5:380–387. 1998, Yang and Huang, Gene Therapy, 4:950–960. 1997). Cationic lipid/DNA complexes activate C but it does not affect in vivo gene transfer (Barron, et al., Human Gene Therapy, 9:315–323. 1998). DNA/cationic lipid complexes made with GL-67 did not activate C because the complexes contain neutral lipids and have charge close to neutrality (Scheule, et al., Human Gene Therapy, 8:689–707. 1997, Plank, et al., Human Gene Therapy, 7:1437–1446. 1996).

Prevention of Unfavorable Interactions

On the basis of the above paradigm, we could borrow from the arsenal of cellular and viral approaches for preventing blood inactivation. For C mediated pathways, a variety of membrane (DAF, MIR1, CR1, MCP) and fluid-phase (C1 inh, C4bp, factor I, factor H) proteins prevent C activation on native cells(Devine and Bradley, Advanced Drug Delivery Reviews, 32:19–29. 1998). Viruses borrow these C inhibitory factors from cells as a "cloak" to prevent C activation. For example, HIV type I uses decay-accelerating factor (CD55) to inhibit C activation (Marschang, et al., Eur. J. Immunol., 25:285–290. 1995). Vectors could incorporate new chimeric or modified C regulatory proteins that are being developed to inhibit C activation (e.g., solubilized C3 convertase inhibitor, modified CD55)(Ryan, Nature Medicine, 1:967–968. 1995).

A "Dysopsonin" hypothesis has been proposed in which serum proteins can bind to foreign particles and prolong their blood circulation(Moghimi, et al., Biochim. BIophys. Acta, 1179:157–165. 1993). For example, Moghimi and colleagues have reported that two serum proteins prevented the uptake of poloxamine (a block co-polymer of polyoxyethylene and polyoxypropylene)-coated microspheres by isolated liver sinusoidal cells but did not identify the proteins. Our preliminary studies indicate that C-reactive protein (CRP) binding to T7 phage can prolong their blood circulation by preventing phage inactivation by C. This work also suggests a new approach for targeting in which natural serum proteins selectively adhere to the delivery particle and provide it with targeting properties.

In terms of artificial delivery systems, incorporation of specific glycoplipids such as GM1 ganglioside, cerebroside sulfate, or phosphatidylinositol or PEG (polyethylene glycol) prolongs the circulation time of liposomes in the blood by providing "steric stabilization"(Lasic and Martin, Pharmacology and Toxicology: Basic and Clinical Aspects, 1995). PEG and other hydrophilic polymers have been incorporated into a variety of polycation- and cationic lipid-containing gene transfer systems (Eastman, et al., Human Gene Therapy, 8:765–73. 1997, Toncheva, et al., Biochim. Biophys. Acta, 1380:354–368. 1998, Wolfert, et al., Human Gene Therapy, 7:2123–33. 1996, Astafieva, et al., FEBS Lett., 389:278–80. 1996, Meyer, et al., J. Biol. Chem., 273:15621–7. 1998, Katayose and Kataoka, J. Pharm. Sci., 87:160–163. 1998, Maruyama, et al., Bioconj. Chem., 8:735–742. 1997, Ferdous, et al., J. Pharm. Sci., 87:1400–1404. 1998, Ferdous, et al., Nucleic Acid Res., 26:3949–3954. 1998, Asayama, et al., Bioconj. Chem., 9:476–481. 1998, Vinogradov, et al., Bioconj. Chem., 9:805–812. 1998, Choi et al., Bioconjugate Chem., 9:708–718. 1998). Despite the promise of PEG, its use can be challenging. For example, it's attachment can interfere with cell surface receptor interactions and endocytosis (Lasic and Martin, Pharmacology and Toxicology: Basic and Clinical Aspects, 1995, Lasic, 1997). PEGylation of adenoviral vectors also interferes with transduction. Sialic acid-containing molecules such as glycophorin (a major RBC sialoglycoprotein), $GM_3$ (a principal sialoglycolipid), GM1 and heparin have been incorporated into liposomes in order to mimic the membrane molecules on cells that inhibit C activation(Okada, et al., Immunology, 48:129. 1983, Okada, et al., J. Immunol., 134:3316. 1985, Michalek, et al., J. Immunol., 140:1581. 1988, Michalek, et al., J. Immunol., 140:1588. 1988, Shichijo and Alving, Biochim. Biophys. Acta., 858:118. 1986). The inhibitory effect of these compounds was abrogated by removal of sialic acid with neuramimidase digestion. Sialic acid surfaces preferentially bind factor H which inhibits the alternative pathway by preventing factor B binding to C3b.

Phage Display Systems, A Powerful Approach for Enhancing Gene Delivery:

The idea of using peptide ligands for targeting drug and gene delivery vehicles (Cotter, M. & Wagner, E. *Receptor-mediated gene delivery strategies*. (eds Friedmann, T.) p. 261–279 (Cold Spring Harbor Laboratory Press, Cold Spring Harbor, 1999)., Reynolds, P. N. & Curiel, D. T. *Strategies to adapt adenoviral vectors or gene therapy applications: Targeting and integration*. (eds Friedmann, T.) p. 111–130 (Cold Spring Harbor Laboratory Press, Cold Spring Harbor, 1999)) and for constructing biocompatible materials (Healy, et al., Ann. N. Y. Acad. Sci., 875:24–35. 1999, Shakesheff, et al., Journal of Biomaterials Science, Polymer Edition, 9:507–18. 1998) is widely accepted due to its conceptual and technical simplicity. A number of peptides with tissue targeting properties were selected both in vitro and in vivo by using the peptide libraries displayed at the amino-terminus of the filamentous phage coat proteins pIII or pVIII (Healy, et al., Ann. N.Y. Acad. Sci., 875:24–35. 1999, Shakesheff, et al., Journal of Biomaterials Science, Polymer Edition, 9:507–18. 1998, Pasqualini and Ruoslahti, Nature, 380:364–6. 1996, Pasqualini et al., Nat. Biotechnol., 15:542–546. 1997, Rajotte, et al., J. Clin. Invest., 102:430–437. 1998, Rajotte and Ruoslahti, J. Biol. Chem., 274:11593–8. 1999, Samoylova and Smith, Muscle Nerve, 22:460–6. 1999, Pasqualini, Quart. J. Nucl. Med., 43:159–62. 1999, Koivunen et al., Meth. Mot. Biol. 129:3–17. 1999, Koivunen et al., Nature Biotech., 17:768–74. 1999, Kassner et al., Biochem. Biophys. Res. Comm., 264:921–8. 1999, Koivunen et al., J. Nuct Med., 40:883–8. 1999, Ivanenkov et al., Biochim. Biophys. Acta, 1448:463–72. 1999, Ivanenkov et al., Biochim. Biophys. Acta, 1448:450–62. 1999, Barinaga, Science, 279:3234. 1998, Arap et al., 279:377–80. 1998, Folkman, Nature Biotech. 15:510).

Libraries of small peptides have been used to map epitopes, protein—protein interactions, protease inhibitors, integrin ligands, and receptor agonists and antagonists (Cwirla, et al., Proc. Natl. Acad. Sci. USA, 87:6378–6382. 1990, Scott and Smith, Science, 249:386–390. 1990, O'Neil et al., Proteins, 14:509–15. 1992, Smith, et al., J. Biol. Chem., 270:6440–9. 1995, Doorbar and Winter, J. Mol. Biol., 244:361–9. 1994, Hong and Boulanger, EMBO J., 14:4714–27. 1995, Ferrer and Harisson, J. Virology, 73:5795–802. 1999, Kola et al., Mol. Immunol., 36:145–52. 1999). Phages displaying larger polypeptides such as antibodies, hormones, enzymes, and DNA-binding proteins have also been screened (Lowman, et al., Biochem., 30:10832–8. 1991, Rebar and Pabo, Science, 263:671–3. 1994, Soumillion, et al., J. Molec. Biol., 237:415–22. 1994, Roberts, et al., Proc. Natl. Acad. Sci. USA, 89:2429–33. 1992).

Of note is the work that is using phage display libraries to develop gene transfer methods (Russell, Nature Med., 2:276–277. 1996). Peptides that bind to shared receptors on different cell lines have been obtained by alternating rounds of biopanning among the different cells (Goodson, et al., Proc. Natl. Acad. Sci. USA, 91:7129–33. 1994). Following injection of a peptide library into the tail vein of mice, brain and kidney-specific peptide sequences were identified and used for specific in vivo targeting of red blood cells (Pasqualini and Ruoslahti, Nature, 380:364–366. 1996). A phage containing the integrin-binding RGD peptide was internalized by cultured human laryngeal epithelial cells (Hart, et al., J. Biol. Chem., 269:12468–12474. 1994). Using bacteriophage, a peptide that binds $\alpha_9\beta_1$-integrin was identified for incorporation into non-viral vectors that are able to transfect airway epithelia (Schneider, et al., FASEB Letters, 429:269–273. 1998). Another group screened an M13 (pIII, 20-mer) library and selected for phage that can be internalized by cells in culture and that had affinity for muscle cells (Barry, et al., Nature Med., 2:299–305. 1996). Recently, bacteriophage libraries were used to identify peptides that can target GST-fusion proteins to lung endothelium (Rajotte, et al., J. Clin. Invest., 102:430–437. 1998). Interestingly, a pIII/M13 27-mer peptide display phage library was used to identify a C3-binding peptide (by panning for C3b-binding phages) that inhibits human C but not rat or mouse C (Sahu, et al., J. Immunol., 157:884–891. 1996).

Of relevance is a study that selected intraperitoneally injected λ bacteriophage for long circulation in the blood (Merril, et al., Proc. Natl. Acad. Sci. USA, 93:3188–3192. 1996). Two bacteriophage clones were selected. One had a glutamic acid to lysine substitution in position 158 (not the carboxy terminus) of the major λ capsid head protein E. Another clone had this same mutation plus an uncharacterized mutation in the λ capsid head protein D. The mechanism by which these mutations enabled prolonged circulation was not characterized.

Methods of Producing Antibodies

The techniques currently used in production of antibodies fall into several groups. The oldest approach uses serum from immunized animals as a source of antibodies The antigen can be injected in different forms, at different locations and at different times into animals of different species. The resultant serum can be used as is or antibodies with a different degree of purity can be isolated from serum using various precipitation, extraction, chromatographic and electrophoretic techniques or their combinations (Harlow and Lane. *Antibodies:a laboratory manual*. Cold Spring Harbor Laboratory Press, Cold Spring Harbor, 1988).

Antibodies can be also produced in vitro, using the hybridoma technology by isolating B-cells from the animals pre-immunized with a particular antigen and growing them in culture. The isolated cells are immortalized by fusing them with myeloma cells that do not produce immunoglobulins of their own. The resultant hybrids are cloned and the clones that secret antibodies against the antigen of interest are selected and propagated further either in culture or as ascites. The secreted antibodies are monoclonal antibodies (Yokoyama WM. Production of monoclonal antibodies. (Eds. Coligan et al.,) *Current Protocols in Immunology*. New York: John Willey and Sons, 1995:2.5.1–2.5.17, Harlow and Lane. *Antibodies:a laboratory manual*. Cold Spring Harbor Laboratory Press, Cold Spring Harbor. 1988,).

An alternative apprach to hybridoma technology is based on the use of gene libraries and expression systems. This allows to avoid labor-intensive immunizations of animals and screening of supernatants. Besides, this approach allows to circumvent tolerance. $V_H$ and $V_L$ libraries are prepared separately and then combined into a combinatorial library by cleaving, mixing and religating the libraries at a restriction site (Huse et al., Science, 246:1275–1281. 1989, Clackson et al., Nature, 352:624–28. 1991). $V_H$ and $V_L$ can both be expressed on one covalent polypeptide (Clackson et al., Nature, 352:624–28. 1991).

The power of the combinatorial approach is considerably enhanced by using phage display libraries, where $V_H$ and $V_L$ genes are expressed on the surface of phage particles as fusion protein with the phage coat protein. This approach permits screening of a large number of sequences (Clackson et al., Nature, 352:624–28. 1991, McCafferty et al., Nature, 348:552–554. 1990). The selection can be started with as many as $10^{10}$ clones prepared from "naive" B-cells. Selected combinations of $V_H$ and $V_L$ genes can be recombined into "hierachic libraries" and selection repeated (McCafferty et al., Nature, 348:552–554. 1990).

The increase in the affinity can also be achieved by mutating selected clones using such techniques as growing phage in the mulD5 *E. coli* strain with an error-prone DNA-polymerase III, "shuffling" of selected sequences, error-prone PCR and site-directed mutagenesis (Low et al., J. Mol. Biol., 260:359–368. 1996, Thompson et al., J. Mol. Biol., 256:77–88 1996).

Another important development in production of monoclonal antibodies was designing antibodies with some or all structure derived from human immunoglobulins. Such antibodies have lower immunogenicity in humans and, therefore, higher therapeutic potential. Several approaches have been taken based of fusion of human cells with animal myelomas or with human tumor cells or immortalization of human cells by using Epstein-Barr virus (Cole et al., Proc. Natl. Acad. Sci., 80:2026–2030. 1983, Olsson and Kaplan, Methods Enzymol., 92:3–16. 1983, Seigneurin et al., Science, 221:173–175). The recombination of selected animal variable regions with human constant regions gives so-called chimeric antibodies (Morrison SL. Science, 229:1202–1207. 1985, Morrison et al., Proc. Natl. Acad. Sci. 81:6851–6855. 1984). The additional substitution of animal framework sequences in the variable regions by human ones gives so called "humanized" antibodies (Jones et al., Nature, 321:522–525. 1986). Some additional engineering work is typically required to optimize the exposure of selected portions of the animal variable region in the new scaffold. Completely human antibodies can be produced now in transgenic mice (Lonberg et al., Nature, 368:856–859. 1994, Green et al., Nat. Genet., 7:13–21. 1994).

Single-stranded antibodies can be produced in a soluble form in *E. coli*. The incorporation of specific, "dimerizing" sequences into single-stranded antibodies with different specificities allows one to produce bispecific antibodies composed of two connected antibody molecules. One of the most powerful uses of such molecules is redirecting cytolytic cells to defined targets (Karpovsky et al., J. Exp. Med., 160:1686–1701. 1984, Titus et al., J. Immunol., 138:4018–4022. 1987). Another interesting application of bi-specific antibodies is changing the viral tropism (Wickham et al., J. Virol., 70:6931–6838).

Uses of Antibodies for Therapeutic Purposes A number of in vivo applications for monoclonal antibodies have been developed (Waldmann TA, Science, 252:1657–62. 1991, Berkower I., Curr. Opin. Biothechnol., 7:622–8. 1988). Leukemias and lymphomas have so far been the favorite targets for in vivo therapy based on the use of monoclonal antibodies (Appelbaum FR., Sem. Hemat., 36(4 Suppl. 6):2–8. 1999, Bendandi and Longo, Curr. Opin. Oncol., 11:343–50. 1999). Numerous attempts to treat other types of cancer have been undertaken as well (Reviewed by Wawrzyczak E J, *Antibody therapy*, Oxford, UK:Bios Scientific Publishers. 1995, Weiner L M., Sem Oncol., 26 (4 Suppl. 14):43–51. 1999, Sem. Oncol. (4 Suppl. 12):41–50). The antibodies can be used either by themselves, relying on the antibody effector functions, or as conjugates with various toxins and radionuclides (Weiner LM., Sem. Oncol., 26 (4 Suppl. 14):43–51. 1999, Sem. Oncol. (4 Suppl. 12):41–50). Antibodies have been also used for a variety of other applications, such as targeting platelets (Gensini et al., Am. Heart J. (2 Pt. 2), 138:171–6. 1999), blocking T-lymphocytes in rejection reactions (Ortho Multicenter Transplant Study Group, N. Engl. J. Med., 313:337–342), intercepting LPS for treatment of sepsis, blocking IL-6 receptor for treatment of multiple myeloma, and membrane IgE for treatment of allergy (Reviewed by Berkower I., Curr. Opin. Biothechnol., 7:622–8. 1988).

Uses of Antibodies for Diagnostic Purposes Most current applications of antibodies serve diagnostic rather than curative purposes. In vitro, they are widely used in RIA and ELISA measurements of substances in biological fluids, from hormones to toxins. They are also indispensable in flow cytometric assays. In vitro, the antigens to be identified are typically fractionated prior to the reaction with antibodies and immobilized on special supports. The antigen-antibody complexes are visualized by using secondary antibodies conjugated with fluorescent or electron-scattering labels or enzymes that digest specific substrate and cause the location precipitation of resultant products. In vivo, antibodies are used as tumor-imaging reagents (Collier et al., Radiology, 185:179–186, 1992).

SUMMARY

The high complexity of available peptide display libraries ($10^7$–$10^9$) should allow the selection of peptides with almost any targeting specificity. Our invention indicates, however, that the behavior of displayed peptides in vivo is more complex than currently realized. We show that immobilized epitopes such as peptides with free carboxy-termini are specifically recognized by natural antibodies and induce rapid activation of complement (C). Recognition of displayed peptides by natural antibodies has not previously been reported. Several possibilities flow from this discovery which include: I) Process of selection for phage that are less prone to inactivation, II) Production of peptide-display phage libraries that are less prone to inactivation, III) Phage that are less prone to inactivation for treating bacterial, IV) Methods for selection of serum proteins that bind specific peptide ligands, V) Peptides for drug and nucleic acid delivery, and VI) Methods for the production and uses of peptide-specific natural antibodies (PSNA).

The selection pressure against T7 phage with displayed peptides in blood provides an unique opportunity for selecting peptides that protect the phage against C by binding to blood proteins. In rat blood, new peptide ligands were identified that protected the phage against C-mediated inactivation by binding C-reactive protein (CRP). In human serum, a number of peptides with tyrosine residues preserved phage infectivity, presumably by binding human $\alpha_2$-macroglobulin.

We have found that an excess of UV-irradiated phage will protect the live phage with the same peptides on the surface against serum inactivation in vitro and in vivo. However, the UV-irradiated phage will not protect live phage with the peptides that have very different structures. In other words, serum inactivation of a specific T7 phage clone is inhibited by an excess amount of UV-irradiated phage from the same class of clones but not from other classes. This indicates that the peptides in the phage library belong to structurally and functionally different classes that activate complement through the interaction with different peptide-binding macromolecules. The differences between distinct classes of peptides may be defined by such parameters as size, shape, charge and hydrophobicity. This also suggests that serum contains a class of molecules that recognizes a specific class of peptides and activates complement (C). Given that the serum was from naive animals or pooled human serum, it could not simply be due to antibodies that arise from immune activation. Use of serum depleted of IgM indicates that it is at least peptide-specific IgM species that recognize the T7 phage clones and activate complement (C). Natural antibodies have been well-described but they are supposed to be "polyreactive" without high-affinity peptide specificity. Thus, it appears that mammals have an innate system for recognizing particles (or surfaces) coated with multiple copies of specific peptides.

Peptide-display phage libraries that are less prone to inactivation can be produced using this knowledge of the inactivation mechanism and the phage (and their associated proteins and peptides) that are resistant to inactivation. For example, a "double-display" phage library can be made so that each phage has two different proteins in its coat; "protein A" that affects its interactions with blood or tissue and "protein B" that contains a "random" peptide sequence. Protein A is derived from the phage clones that are selected for persistence in circulation in animals and for resistance to inactivation in serum in vitro or in vivo.

This recognition process based upon peptide-specific natural antibodies (PSNA) and complement activation may also play a role in normal and pathologic processes. For example, protease digestion of viruses, cell surfaces or internal structures (e.g. myofibers, myelin or joint surfaces) may lead to the display of several carboxy terminated peptides that are likely to be recognized by peptide-specific IgM. This could be beneficial in the clearance of viruses but destructive in tissues such as joints or myelin.

The discovery of peptide-specific natural antibodies (PSNA) has several important applications. PSNA's can be purified from the sera of humans or animals or be produced recombinantly. These PSNA's can be used for diagnostic purposes for detecting a variety of disorders in humans and other living organisms (animals and plants and microogranisms) that include infectious disease, auto-immune disorders and disorders with an autoimmune component (such as rheumatoid arthritis, systemic lupus eryth-rematosus (SLE), multiple schlerosis, ankylosing spondylitis, psoriasis, Reiter's Syndrome, fibromylagia, dermatomyositis, polymyositis, schleroderma, diabetes mellitius, glomerulonephritis), and cancer. These PSNA's could also be used to treat human and animal disorders that include cancer, infectious disease, auto-immune disorders and aspects of other disorders.

Figure 1:
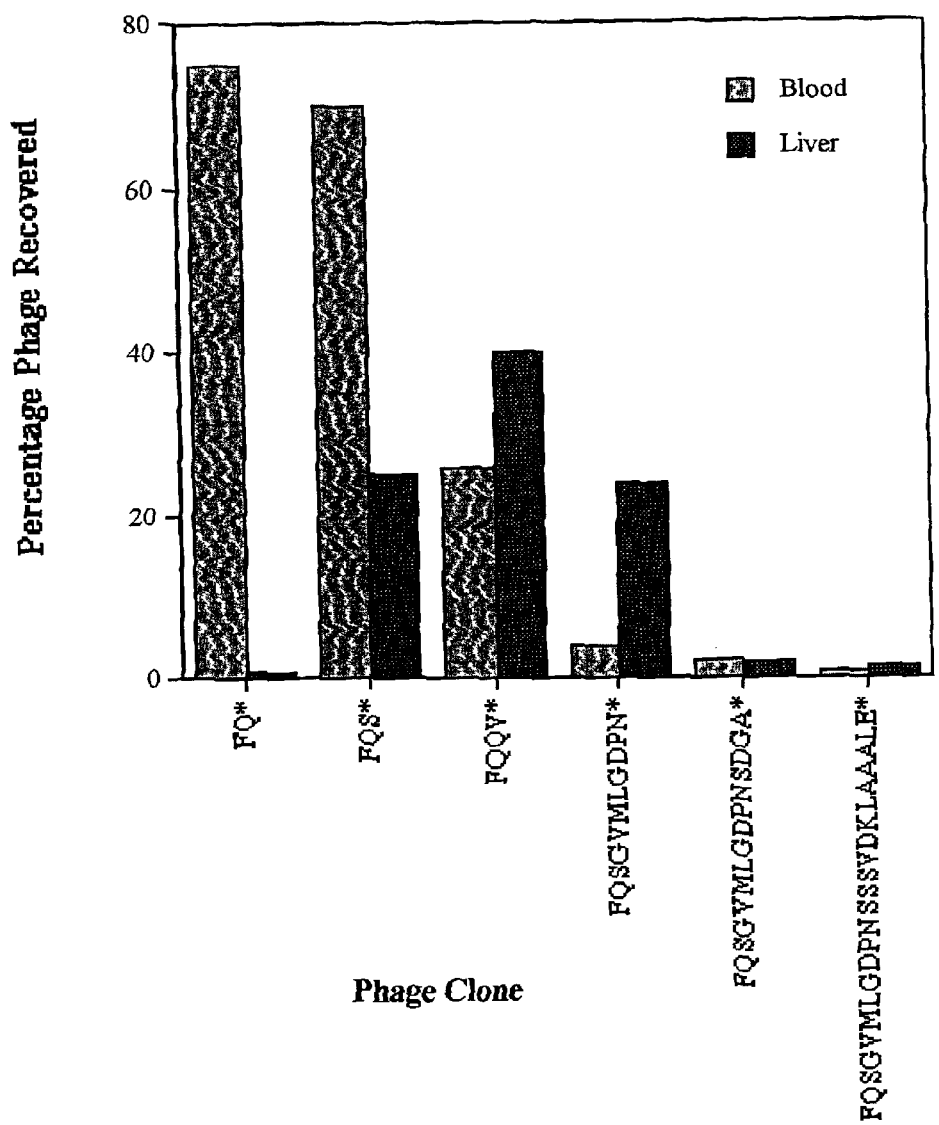
FIG. 1. The percentage of phage recovered (phage recovered/phage injected X 100, mean of 2 experiments) of various T7 phage clones from the blood and liver 5 min after tail vein injections in mice in vivo. Our laboratory names for the T7 phage corresponding to their C-terminus sequences are shown below. T7 vector refers to the vector coding sequence without any library inserts.

Methods: The phages (109 pfu/0.3 ml PBS) were injected into tail vein of ICR male mice (5–6 weeks old) pre-treated (20–24h) with GdCl3 at a dose of 10 mg/kg. Three min after injection, heparin (20 unit/head) was injected by same route. Under anesthesia, blood was collected directly from heart and livers were perfused with 1 unit heparin/ml containing PBS 30 ml for 3 min, and then collected. Livers were homogenated with 3-fold of their weight of 2% Triton X-100/1M NaCl in PBS to lyse the cells and disperse the phage. The titration of phages was assessed by using *E. coli* BL21 in an appropriate dilution.

20/6 FQ*

32/77 FQS*

32/23 FSQV*

112 FQSGVMLGDPN*

114 . . . FQSGVMLGDPNSDGALRQSGRGKSSRP*

T7 Vector FQSGVMLGDPNSSSVDKLAAALE*

DETAILED DESCRIPTION

The invention is described in the following sections: I) Methods of selection for phage that are less prone to inactivation, II) Peptide-display libraries and production of peptide-display phage libraries that are less prone to inactivation, III) Phage that are less prone to inactivation for treating bacterial infections, IV) Methods for selection of serum proteins that bind specific peptide ligands, V) Peptides for drug and nucleic acid delivery, infections, VI) Methods for the production and uses of peptide-specific natural antibodies (PSNA).

I. Methods of Selection for Phage That Are Less Prone to Inactivation

We have discovered that bacteriophage (abbreviated as "phage") are inactivated in blood in vivo (e.g., in the systemic circulation of an animal) and in serum in vitro (in a test tube outside of the body) by natural antibodies and complement. The test tube indicates any type of container for holding a liquid and can be made of glass or plastic. Inactivation means the loss of the phage's ability to infect bacteria. Phage infection can be assessed based on the ability of phage to lyse bacterial lawns. Therefore, the amount of phage is expressed in plaque forming units that correspond to the number of plaques (small clear areas) in a lawn of bacteria grown on an agar plate.

The phage can be inactivated by antibodies that activate complement upon binding to the phage. The antibodies can be natural antibodies that mostly belong to the IgM or IgG class. The phage can also be inactivated if it is biotinylated prior to exposure to the bodily fluid (e.g., blood in vivo or in vitro) and then allowed to interact with a probe that tightly binds biotin, such as avidin, streptavidin, neutravidin, or other protein derived from or related to these proteins.

In one embodiment of the invention, this inactivation process is used to select for phage that are resistant to the inactivation process. The initial phage for this selection process can be (but not limited to) peptide display phage libraries that are derived from filamentous phage such as M13 or non-filamentous phage such as T7 phage. The initial phage can also be UV-irradiated to increase the number of mutations or derived from recombinant DNA that has been subjected to regular polymerase chain reaction (PCR), error-prone PCR, or DNA shuffling or method to increase the variability or number of mutations in the phage sequence.

For the in vitro testing, blood or a blood derived material such as plasma, serum, or purified proteins and factors can be used in the inactivation process. For the in vitro testing, serum derived from blood (by clotting) or citrated plasma (by adding Ca) can be used in the inactivation process. The complement-grade serum from commercial sources that is pre-filtered and lyophilized or snap-frozen can also be used. Prior to use, the serum pH can be left as is or adjusted to 7.2–7.6. In case of commercial serum, it is also filtered to remove protein precipitate formed during freezing or lyophilization. With the serum depleted of particular proteins, purified proteins such as immunoglobulins (Ig) as a whole or Ig fractions that are enriched for IgG, IgM, IgA, or IgD can be used to reconstitute the ability of serum to inactivate phage. Purified factors that may be required for phage inactivation or protection by incomplete serum also include complement proteins, blood fractions containing proteins greater than 25 kDa (kilodaltons) 50 kDa, 100 kDa, 200 kDa or 300 kDa in size. Blood, serum, plasma, or other blood-derived fractions can be subjected to purification processes that include precipitation, extraction, column chromatography methods and electrophoresis. Column chromatography methods include the following types of chromatography: size exclusion, ion-exchange, reverse phase, affinity purification or any combination of these types. Electrophoresis includes the types of separation based on charge, pI, the change of protein mobility in the presence of particular ligands or any combination of these techniques.

For in vivo testing in the whole animal, the phage can be injected intravenously or intraarterially into the systemic or pulmonary circulation. It can also be injected into blood vessels that supply the liver (hepatic artery, portal vein, hepatic vein, via the vena cava, via the aorta), kidneys, muscle (femoral, iliac, brachial, axilla arteries) or brain. The phage can also be injected into other body spaces that include the peritoneum (intraperitoneally) and cerebral spinal fluid (ventricular spaces, sub-dural, epidural). The animal can be a vertebrate such as fish, amphibians, reptiles or mammals. Mammals include rodents (mice, rats), guinea pigs, hamsters, dogs, pigs, non-human primates (such as Rhesus) and humans. The animals can be particular strains with certain features. These can be animals that are defective in the immune system and do not produce certain antibodies, for instance, IgM-deficient mice. These animals can also have defects in the complement system, such as the absence or functional impairment of particular complement proteins caused by natural or artificial deletions or mutations in the corresponding genes.

Phage that are resistant to inactivation can be obtained from a variety of tissues in vivo, including the blood, liver, lung, brain, muscle, spleen, kidneys, intestines, prostate, thymus, adrenal glands, thyroid, gonads, eyes, and skin. The resistance to inactivation results from association of phage with particular plasma proteins that protect phage against inactivation by the complement system. Different plasma proteins bind to phage through specific recognition of different peptides or proteins or protein domains displayed at the phage surface. Such complexes of phage with plasma proteins can either stay in circulation or be targeted to particular locations through the interaction of bound plasma proteins with cell receptors. The binding of bound plasma proteins to cell receptors is promoted by changes in the conformation of bound proteins and by a high level of cooperation on the protein-receptor interactions due to a high density of bound proteins on the phage surface. Therefore, the phage binds to particular organs through indirect targeting. Alternatively, if the peptides are exposed on the phage in the format that is not recognized by natural antibodies, the phage can be used to select for the peptides that bind to cell receptors directly.

In one embodiment to measure the survival of phage T7 in blood, $10^9$ pfu of phage per animal are injected into a tail vein and 100 µl blood samples are collected from a non-injected tail vein (of the same animal) into 10 µl (10U) of heparin on ice at specified time points. Plasma is prepared by centrifugation. Phage from blood and plasma are detected by soft agar plating. Plating dilutions are done in LB medium (20 g of yeast extract, 40 g of trypton and 20 g of NaCl per 1L of medium).

In a preferred embodiment, phage are subjected to more than one round of selection. Phage that are selected for resistance to inactivation are then grown on bacteria to expand their number and then subjected to another inactivation process. This can change the type of phage clones that are resistant to inactivation. It can also increase the percentage of phage that survive the inactivation process.

In other embodiments, factors that affect the inactivation process can be added to the test tube in vitro or to the living animal. These include small molecules or drugs such as phosphoryl choline and aminocaproic acid. Molecules that inhibit macrophage activity include gadolinium ($GdCl_3$), carrageenan and incapsulated bisphosphonates. Molecules that inhibit the complement system include antibodies, venoms (e.g cobra venom factor—CVF) and natural or artificial complement regulatory proteins represented by both membrane and soluble proteins. The function of the complement system in vitro can be also inhibited by heat (50° C. for the alternative complement activation pathway and 56° C. for the classical complement activation pathway) and chelators (EGTA or EDTA for the alternative complement activation pathway and EDTA or EGTA or EGTA/Mg for the classical complement activation pathway).

II. Peptide-Display Libraries and Production of Peptide-Display Phage Libraries That Are Less Prone to Inactivation T7-based peptide display libraries are made by using Novagen T7 vectors. Both the vectors that give the phage with a high number of peptide copies per phage particle (displayed in all coat proteins) and the vectors that give just 0.1–10 copies of peptides of polypeptides per phage particles are used. Low-copy phage are grown either in the *E. coli* strains provided by Novagen (BLT5403 and BLT5615) or other strains. The bulk of the phage coat protein comes from the plasmid but the structure of this protein is different. The *E. coli* strains BLT5403 and BLT5615 produce T7 protein 10A. In other libraries, the bulk of the phage coat protein is a truncated 10B protein that shows a remarkable protection of phage against complement-mediated inactivation.

"Double" display libraries displaying: a) a "constant" peptide or protein that prevents serum inactivation (e.g. lys+/arg+peptides) or is less prone to inactivation and b) a random peptide for selection of tissue, sub-cellular, or blood persistence properties.

For making "double" display libraries of T7 phage, bacteria such as *E. coli* are modified so that it expresses a T7 phage coat protein that is incorporated into phage that constitute a peptide-display library. It is double-display in that each phage has two different proteins in its coat; "protein A" that affects its interactions with blood or tissue and "protein B" that contains a "random" peptide sequence. This peptide sequence is "random" in that it is different among different phage clones that constitute a phage library. In one embodiment, protein A is selected for resistance to serum inactivation in vitro or prolonged blood circulation in vivo. In one embodiment protein A is derived from the phage clone 20-6 (Table 3) (AAGAVVFQ peptide sequence for coat protein carboxy-terminus).

Selected sequence:
MASMTGGQQMGTNQGKGVVAAGDKLA-LFLKVFGGEVLTAFARTSVTTSRH
MVRSISSGKSAQFPVLGRTQAAYLAP-GENLDDKRKDIKHTEKVITIDGLLTAD
VLIYDIEDAMNHYDVR-SEYTSQLGESLAMAADGAVLAEIAGLCNVESKYNEN
IEGLGTATVIETTQNKAALTDQVAL-GKEIIAALTKARAALTKNYVPAADRVFY
CDPDSYSAILAALMPNAANYAALIDPE-KGSIRNVMGFEVVEVPHLTAGGAGT
AREGTTGQKHVFPANKGEGNVKVAKDN-VIGLFMHRSAVGTVKLRDLALERA
RRANFQADQIIAKYAMGHGGLRPEAAGAVVFQ In other embodiments, protein A is derived from the phage clone 32-77 (AAGAVVFQS peptide sequence for coat protein carboxy-terminus) or phage clone 32-23 (AAGAVVFSQV peptide sequence for coat protein carboxy-terminus) (Table 3). In yet other embodiments, protein A is derived from phage clones listed in Table 1 and have a terminal lysine (Table 1A) or arginine (Table 1B) or contain a tyrosine (Table 1E). The gene encoding these different "protein A" are placed within a plasmid that is carried by a bacteria such as *E. coli*.

"Protein B" contains a "random" peptide sequence. This peptide sequence is "random" in that it is different among different phage clones that constitute a phage library. The random peptide sequence can be at the amino terminus, carboxy terminus or within the coat protein. The random peptide sequence can encode a peptide that is one to 25 amino acid residues in length. The random peptide can contain invariant parts in addition to the random part. In one embodiment, the invariant part is derived from phage clones listed in Table 1 and has a terminal lysine (Table 1A) or arginine (Table 1B) or contains a tyrosine (Table 1E).

T7 phage libraries constructed with proteins "A" and "B" can have varying proportions of these proteins. In one embodiment, protein A constitutes 0.1, 1, 10, 20, or 50 percent of the coat proteins in the phage. Proteins A and B can contain two cys residues so that disulfide bonds are formed and peptide sequences are constrained.

In one embodiment, T7 libraries displaying random peptides within the 10B capsid protein are constructed using a random one- to 25-mer peptide insert by using simple second strand synthesis (O'Neil, et al., Methods in Enzymology, 245:370–86. 1994) and placed into the Eco RI/Hind III sites of the T7Select 415-1 vector arms (Novagen Corp., Madison, Wis.). The single-stranded sequence is an oligonucleotide (xxxGAATTCggacggtgcc (NNG/T) 1–25 ggggctggaAAGCTTxxxxxx). A 21-mer reverse primer (xxxxxAAGCTTtccagcccc) is used to fill in the complementary strand with exo⁻ Klenow fragment. Specific methods for cloning, propagation and maintenance are used as specified in the manual supplied with the T7Select Kit (Novagen). The complexity of our libraries generated by growing phage in the BL21 *E. coli* strain is determined.

In order to be able to draw on long peptides, along with short ones, two other *E. coli* host strains, BLT5615 and BLT5403 in addition to BL21m can be used. Both strains provide additional phage T7 coat protein, 10A, from a plasmid. According to our observations, the ratio of 10A and 10B proteins in the phage based on the vector T7Select415-1is 4 to 1. A lower density of long peptides on the phage surface promotes phage survival in a mixed population. Decreasing the density of displayed peptides should be also useful while trying to select for high-affinity peptide ligands. It enables one to determine the number of peptides required for a certain effect.

Constrained phage T7 display containing $X_2CX_{3-20}CX_2$ peptides can also be used. It may be necessary to expose the phage to gentle oxidizing agents to form the disulfide bonds. It has been found that constrained peptide display libraries may be more apt for finding a specific ligand but this may not be necessary for large peptides that can form secondary structure.

III. Phage for Treating Bacterial Infections

Peptide-display phage that are less prone to inactivation can be used to treat bacterial infections. In one embodiment, a phage library is selected for clones that are resistant to serum inactivation in vitro and the clones resistant to serum inactivation are injected into an animal with a bacterial infectious disorder. The phage infects the bacteria and kills the bacteria, thus alleviating the infectious disease state in the animal. The phage can be injected intravenously or into the tissue that is infected such as sinuses, pulmonary, prostate, gastrointestinal, or central nervous system (ventricular fluid, brain parenchyma, spinal cord). In one embodiment, the phage is a T7 phage. In another embodiment, the T7 phage is the phage clone 20-6 (Table 3) (AAGAVVFQ peptide sequence for coat protein carboxy-terminus).

IV. Selection of Serum Proteins That Bind Specific Peptide Ligands

We have discovered that phage are rapidly inactivated by blood, serum and other blood derivatives and factors in vitro and in the circulating blood in vivo. Phage clones can be selected that are resistant to this inactivation process. In some instances, the phage clones that are resistant to inactivation bind to blood constituents such as serum proteins. In a preferred embodiment a blood constituent binds to the displayed peptide sequence that is unique or specific to that particular phage clone. (That is, each phage clone displays a specific peptide sequence that is related to a DNA sequence and that is specific to the specific phage clone. Depending on the complexity of the phage library the phage clone and thus the peptide sequence may or may not be unique.)

The blood constituent that binds to the peptide (cognate to the phage clone that is resistant to inactivation) can be purified and identified on the basis of the affinity of the blood constituent for the peptide. In one embodiment, affinity purification can be accomplished by affinity chromatography.

Yet in another embodiment, affinity purification can be done by affinity centrifugation. In another embodiment, affinity purification can be performed using affinity precipitation. For example, antibodies against the phage can be used to immunoprecipitate the phage with the blood constituent attached to the phage. In another embodiment, affinity purification can be brought about by filtering. In one instance, filters that do not let the phage pass through filters can be used to purify the phage and the blood constituent attached to it away from the rest of the blood constituents that do notbind the phage as tightly.

In all these types of affinity purification, the phage can be washed to enrich for a blood constituent that binds the phage clone with different affinities or via different methods. The washes can contain various concentrations of salt. The washes can also contain detergents. The washes can also contain specific ligands such as phosphatidyl choline, free peptides, and peptides attached to proteins and other supports.

In a preferred embodiment, after the blood constituent and the phage are purified from the rest of the blood, the blood constituent bound to the phage is separated from the phage and the blood constituent is identified using techniques such as protein gel electrophoresis, two-dimensional electrophoresis, immunoblotting, and protein sequencing.

V. Peptides for Biologically-active Compound and Nucleic Acid Delivery

Phage clones that are resistant to inactivation can be used to derive peptides that are of use for drug and nucleic acid delivery. In one embodiment, they are peptides that have a terminal lysine or arginine at the carboxy terminus. In another embodiment, they are peptides that contain a tyrosine. In yet another embodiment, they are peptides that have a terminal lysine or arginine at the carboxy terminus or they are peptides that contain a tyrosine and that are used to prolong the circulation life or persistence of the biologically-active compound or nucleic acid delivery particle in the circulation or render the drug or nucleic acid delivery particle more resistant to inactivation.

In still another embodiment, the peptide contains a cell targeting signal and a terminal lysine or arginine at the carboxy terminus. The peptide can also contain a cell targeting signal and a tyrosine. The peptides that contain a cell targeting signal and a terminal lysine or arginine at the carboxy terminus and that are used to prolong the circulation life or persistence of the biologically-active compound or nucleic acid delivery particle in the circulation or render the drug or nucleic acid delivery particle more resistant to inactivation.

A biologically-active compound or nucleic acid delivery particle consists of a biologically-active compound or nucleic acid and amphipathic compounds. In another embodiment, the drug or nucleic acid delivery particle can consist of a drug or nucleic acid and liposomes. Also, the drug or nucleic acid delivery particle can consist of a drug or nucleic acid and a polymer. The polymer can be a polyion such as a polycation or polyanion. Yet in another embodiment, the drug or nucleic acid delivery particle can consist of a drug or nucleic acid, an amphipathic compound, and a polymer. Still in another embodiment, the peptide could have the carboxy terminus blocked so that there is not unmodified carboxy group at the "carboxy" terminus or the peptide could have the amino terminus blocked so that there is no unmodified amino group at the "amino" terminus.

In yet another embodiment, random peptides or the peptides with the primary structure corresponding to the primary structure of the proteins from the recipient species are used to target nucleic acids or drug carriers to the liver. Also, the delivery particles derivatized with random peptides or the peptides with the structure derived from the proteins of the recipient species are used to decrease immunogenicity of conjugated peptides.

VI. Peptide-specific Natural Antibodies

Peptide-specific natural antibodies (PSNA) are natural antibodies that reacts specifically with a peptide in some demonstrable way such as inducing inactivation of phage that display multiple peptides. It can also be demonstrated by enzyme linked immunoassay (ELISA) or radioimmunoassay (RIA) or by affinity chromatography.

In one embodiment, the PSNA's are IgM or IgG.

In another embodiment, PSNA's are purified from serum or plasma by using synthetic peptides conjugated to the resin. The PSNA's bound to the peptides on the column can be eluted by low pH or high pH buffers, by the buffers containing chaotropic agents or high salt or by the buffers that combine any of these properties. The PSNA's with low affinity can be isolated by isocratic elution of the column with the same buffer that was used to apply serum or plasma on to the column.

In another embodiment, PSNA's are produced using recombinant methods-include phage as well. $V_H$ and $V_L$ immunoglobulin genes are isolated from a pool of "naive" B-cells and used to construct single-chain antibodies exposed either on M13 or T7 phage. The phage is panned against UV-inactivated, immobilized T7 phage displaying specific peptides or a whole library. Alternatively, the phage is panned against immobilized synthetic peptides. The bound live phage is collected and amplified. The selection process is repeated and selected immunoglobulins characterized in terms of their affinity toward target peptides and the ability to activate C if converted into a physiological form recognized by C1q.

In yet another embodiment, PSNA's can be produced using monoclonal methods. B-cells producing PSNA's are be selected by using fluorescently labeled phage displaying peptides of interest. The selected B-cells are immortalized using conventional techniques, cloned and the antibodies secreted by resultant clones are characterized for their ability to bind peptides of interest and activate C once bound.

In another embodiment, PSNA-producing B-cells are selected by using antiidiotypic antibodies that specifically bind to PSNA's.

PSNA's can be used for diagnostic or detection purposes. These include detecting the presence of a particular peptide sequence in a protein. The protein containing the specific peptide sequence or a peptide can be in a mixture such as in an extract from a tissue or a tissue section. The protein or peptide can be on a membrane, glass, or plastic structure. The protein or tissue section could be first digested with an enzyme and then probed with the PSNA. Binding of the PSNA to the peptide sequence can be detected by a variety of methods. These include the attachment of a reporter or marker molecule directly to the PSNA or indirectly. In one embodiment, another antibody or secondary antibody containing a reporter or marker molecule is used to detect the presence of the PSNA. The PSNA can be used in immunoblots, ELISA, RIA, immunohistochemical assays, fluorescence polarization, or Biocore-type binding assays.

PSNA's can also be used for selective visualization or labeling of particular issues or cells. PSNA's can be indirectly selected for this purpose from a natural pool of PSNA's or from B-cell libraries by using the phage that displays a repertoire of peptides characteristic of certain cells or tissues. Such phage can be selected by pre-incubating serum with the cells or tissues of interest followed by collecting the phage that survives in the serum pre-incubated with the target tissue. Prior to these steps, the target cells can be pre-treated with proteases that would generate exposed protein carboxy-termini or permeabilized with detergents or fixed and then permeabilized with detergents. The treatment of cells with detergent is used to expose protein carboxy-termini on the inner side of the cell plasma membrane and on the cell organells. A combination of proteolysis and permeabilization can also be used. The pre-existing and/or protease-generated repertoire of carboxy-termini on the plasma membrane and cell organelles can be different for different types of cells. Therefore, different PSNA's would be removed from the serum pre-exposed to different cells. The phage displaying corresponding peptides would survive in the absence of cell- or tissue-specific PSNA's and could be used after a few rounds of selection as a probe for the isolation of B-cells producing PSNA's against these peptides. Corresponding synthetic peptides could be used for affinity purification of preexisting PSNA's that would selectively react with different cells and tissues. The staining of cells or tissues with selected PSNA's can be done using conventional secondary antibodies or by using the antibodies against C proteins. In the latter case, the complement deposition will be specifically induced by the multivalent binding of PSNA's to closely spaced protein carboxy-termini. Spurious binding events will not generate complement activation and, therefore, will not be detected.

A similar approach can be used to generate PSNA's that would stain particular protein bands or spots immobilized on paper, plastic or glass supports. The immobilized proteins could be incubated with serum as is or after mild treatment with proteases. The serum depleted of particular PSNA's would be used to select phage with corresponding peptides.

The different individual types of PSNA's can be correlated with the prevalence, incidence, penetration, or likelihood of an individual having a specific disease or disorder. This would be akin to correlating a particular genotype to a phenotype. In fact, the genetic loci for encoding the PSNA's could be used for this purpose as well.

PSNA's can also be used to treat disease in living creatures and organisms such as animals and humans. The disease can be, but not limited to, an infectious disease, cancer, autoimmune disorder, inflammatory condition, cardiovascular disorder, or nervous disorder. The PSNA can be injected into the blood or a tissue. It can be a part of the PSNA such as the part the binds the peptide. The PSNA that is used for therapeutic purposes can be purified from a bodily fluid, produced by recombinant methods, or by "monoclonal" methods. The PSNA can be "humanized" in that parts of the PSNA that are non-essential for binding to the peptide are removed and replaced with parts of human antibodies. The PSNA can also be linked to another biologically-active compound or protein such as a toxin (e.g., diptheria or pertusis)

Definitions

To facilitate an understanding of the present invention, a number of terms and phrases are defined below:

Biologically Active Compound

A biologically-active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. In this specification, the cellular production of, or inhibition of a material, such as a protein, caused by a human assisting a molecule to an in vivo cell is an example of a delivered biologically active compound. Pharmaceuticals, proteins, peptides, polypeptides, hormones, cytokines, antigens, viruses, oligonucleotides, enzymes and nucleic acids are examples of biologically active compounds.

Peptide and polypeptide refer to a series of amino acid residues, more than two, connected to one another by amide bonds between the alpha-amino group and carboxyl group of contiguous amino acid residues. The amino acids may be naturally occurring or synthetic. Polypeptide includes proteins and peptides, modified proteins and peptides, and non-natural proteins and peptides. Enzymes are proteins evolved by the cells of living organisms for the specific function of catalyzing chemical reactions. A chemical reaction is defined as the formation or cleavage of covalent or ionic bonds. Bioactive compounds may be used interchangeably with biologically active compound for purposes of this application.

Delivery of Biologically-Active Compound

The delivery of a biologically-active compound is commonly known as "drug delivery". "Delivered" means that the biologically-active compound becomes associated with the cell or organism. The compound can be in the circulatory system intravessel, extracellular, on the membrane of the cell or inside the cytoplasm, nucleus, or other organelle of the cell.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, and bile ducts. The intravascular route includes delivery through the blood vessels such as an artery or a vein. An administration route involving the mucosal membranes is meant to include nasal, bronchial, inhalation into the lungs, or via the eyes. Other routes of administration include intraparenchymal into tissues such as muscle (intramuscular), liver, brain, and kidney. Transdermal routes of administration have been effected by patches and ionotophoresis. Other epithelial routes include oral, nasal, respiratory, and vaginal routes of administration.

Nucleic Acid

The term "nucleic acid" is a term of art that refers to a polymer containing at least two nucleotides. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and synthetic derivatives of purines and pyrimidines, or natural analogs. Nucleotides are the monomeric units of nucleic acid polymers. A "polynucteotide" is distinguished here from an "oligonucleotide" by containing more than 80 monomeric units; oligonucleotides contain from 2 to 80 nucleotides. The term nuclei acid includes deoxyribonucleic acid (DNA) and ribonucleic acid (RNA). The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

DNA may be in the form of anti-sense, plasmid DNA, parts of a plasmid DNA, product of a polymerase chain reaction (PCR), vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups.

"Anti-sense" is a polynucleotide that interferes with the function of DNA and/or RNA. This may result in suppression of expression. Natural nucleic acids have a phosphate backbone, artificial nucleic acids may contain other types of backbones and bases. These include PNAs (peptide nucleic acids), phosphothionates, and other variants of the phosphate backbone of native nucleic acids. In addition, DNA and RNA may be single, double, triple, or quadruple stranded.

The term "recombinant DNA molecule" as used herein refers to a DNA molecule that is comprised of segments of DNA joined together by means of molecular biological techniques."Expression cassette" refers to a natural or recombinantly produced polynucleotide molecule that is capable of expressing protein(s). A DNA expression cassette typically includes a promoter (allowing transcription initiation), and a sequence encoding one or more proteins. Optionally, the expression cassette may include trancriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

A nucleic acid can be used to modify the genomic or extrachromosomal DNA sequences. This can be achieved by delivering a nucleic acid that is expressed. Alternatively, the nucleic acid can effect a change in the DNA or RNA sequence of the target cell. This can be achieved by homologous recombination, gene conversion, or other yet to be described mechanisms.

Gene

The term "gene" refers to a nucleic acid (e.g., DNA) sequence that comprises coding sequences necessary for the production of a polypeptide or precursor (e.g., -myosin heavy chain). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

Gene Expression

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Delivery of Nucleic Acids

The process of delivering a polynucleotide to a cell has been commonly termed "transfection" or the process of "transfecting" and also it has been termed "transformation". The polynucleotide could be used to produce a change in a cell that can be therapeutic. The delivery of polynucleotides or genetic material for therapeutic and research purposes is commonly called "gene therapy". The delivery of nucleic acid can lead to modification of the DNA sequence of the target cell.

The polynucleotides or genetic material being delivered are generally mixed with transfection reagents prior to delivery. The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA. The term "naked polynucleotides" indicates that the polynucleotides are not associated with a transfection reagent or other delivery vehicle that is required for the polynucleotide to be delivered to a cell.

A "transfection reagent" or "delivery vehicle" is a compound or compounds that bind(s) to or complex(es) with oligonucleotides, polynucleotides, or other desired compounds and mediates their entry into cells. Examples of transfection reagents include, but are not limited to, cationic liposomes and lipids, polyamines, calcium phosphate precipitates, histone proteins, polyethylenimine, and polyl-ysine complexes (polyethylenimine and polylysine are both toxic). Typically, when used for the delivery of nucleic acids, the transfection reagent has a net positive charge that binds to the polynucleotide's negative charge. For example, cationic liposomes or polylysine complexes have net positive charges that enable them to bind to DNA or RNA.

Polymer

A polymer is a molecule built up by repetitive bonding together of smaller units called monomers. A polymer is defined as a compound containing more than two monomers. A monomer is a compound that can be attached to itself or another monomer and thus a form a polymer.

In this application, the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

Polyion

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers. The term zwitterionic refers to the product (salt) of the reaction between an acidic group and a basic group that are part of the same molecule.

Cell Targeting Signals

Cell targeting signal (or abbreviated as the Signal) is defined in this specification as a molecule that modifies a biologically active compounds such as drug or nucleic acid and can direct it to a cell location (such as tissue) or location in a cell (such as the nucleus) either in culture or in a whole organism. By modifying the cellular or tissue location of the foreign gene, the function of the biologically-active compound can be enhanced.

The cell targeting signal can be a protein, peptide, lipid, steroid, sugar, carbohydrate, (non-expresssing) polynucleic acid or synthetic compound. The cell targeting signal enhances cellular binding to receptors, cytoplasmic transport to the nucleus and nuclear entry or release from endosomes or other intracellular vesicles. The cell targeting signal can be a ligand that binds to its cognate receptor.

Nuclear localizing signals enhance the targeting of the pharmaceutical into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta.The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. These include a short NLS (H-CGYGPKKKR-KVGG-OH) or long NLS's (H-CKKKSSSDDEATADS-QHSTPPKKKRKVEDPKDFPSELLS-OH and H-CKKK-WDDEATADSQHSTPPKKKRKVEDPKDFPSELLS-OH). Other NLS peptides have been derived from M9 protein (CYNDFGNYNNQSSNFGPMKQGNFGGRSSGPY), E1A (H-CKRGPKRPRP-OH), nucleoplasmin (H-CKKAVKRPAATKKAGQAKKKKL-OH), and c-myc (H-CKKKGPAAKRVKLD-OH).

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides.

Cellular receptor signals are any signal that enhances the association of the biologically active compound with a cell. This can be accomplished by either increasing the binding of the compound to the cell surface and/or its association with an intracellular compartment, for example: ligands that enhance endocytosis by enhancing binding the cell surface. This includes agents that target to the asialoglycoprotein receptor by using asioglycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

Amphipathic Compounds

Amphipathic compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Peptides

Peptides are polymers of amino acid residues and their derivatives. The peptide contains 1or more amino acids and can be synthesized by artificial synthetic methods or in a living organism. The amino acid residues are joined by peptide bonds. A peptide bond is one which the carboxy group of one amino acid is united with the amino group of another amino acid, with elimination of a molecular of water, thus forming a peptide bond: —CO—NH—. The peptide can contain amino acid derivatives or analogs such as d-forms of amino acids or β-amino acids.

Blood and Its Constituents

According to Stedman's dictionary, blood is the "fluid and its suspended formed elements that circulated through the heart, arteries, capillaries, and veins. The constituents of the blood are the non-cellular parts: serum, plasma, and the cellular parts: red blood cells, white blood cells (leukocytes), and platelets. Plasma is the fluid (non-cellular) part of the blood of the blood that is distinguished from the serum obtained after coagulation. Serum is the fluid portion of the blood after removal of the fibrin clot and blood cells, distinguished from the plasma in circulating blood. The non-cellular parts of blood also consist of complement and clotting factors. A blood product is a substance that is formed from blood or purified from blood.

Complement (C)

It is a thermolabile substance, normally present in serum, that is destructive to certain bacteria and other cells which have been sensitized by specific complement-fixing antibody. The C system comprises more than 30 plasma or membrane proteins. The activation of C relies on a cascade of proteolytic steps performed by the protease domains in the components involved. There three distict C activation pathways: the classical pathway triggered by target-bound antibody, the MBLectin pathway triggered by polysaccharide structures of microbes, and the alternative pathway triggered by the recognition of exogenous structures by the C components themselves. For historical reasons, the components of the C system are numbered from C1 to C9, with the biochemical reaction sequence being C1-C4-C2-C3-C5-C6-C7-C8-C9.

C1 (a complex of three subunits, C1q, C1r, and C1s) after activation by antibody-antigen complex or other activators is enzymic (as C1 esterase) for C4 and (owning to the reaction with C4) for C2. The C42 moiety (C3 convertase) of the C142 complex then cleaves C3, the active fragment of which enters the C1423 complex that cleaves C5. The complex C14235 then combines sequentially with C6, C7, C8, and C9 for form lytic complemnt. C1 may be activated also by aggregated antibody. C3 may also be activated by bacterial endotoxin, by the properdin system, and by a component of cobra venom.

Antibodies

One or other classes of globulins (immunoglobulins) present in the blood serum or-body fluids of an animal. The classes include IgG, IgM, IgA, IgD and IgE.

Natural Antibodies

Natural antibodies are antibodies whose appearance in the blood does not require immunization with the corresponding antigen. According to Stedman's Medical Dictionary (Williams and Wilkins Co., Baltimore-23rd edition, 1976), "Originally, antibody was a body or substance evoked in man or other animal by an antigen, and characterized by reacting specifically with the antigen in some demonstrable way- antibody and antigen each being defined in terms of the other, but it is now supposed that antibodies may also exist naturally without being present as a result of the stimulus provided by the introduction of an antigen.

Phage

Phage is also known as bacteriophage and is a virus that infects bacteria or has an affinity for bacteria. They can contain either DNA or RNA. They may contain either single- or double-stranded nucleic acid. They can have various shapes and sizes. They can use different bacterial strains or species as a host. They can lyze the infected cells or just use the cells for reproduction.

Reporter or Marker Molecules

Reporter or marker molecules are compounds that can be easily detected. Typically they are fluorescent compounds such as fluorescein, rhodamine, Texas red, cy 5, cy 3 or dansyl compounds. They can be molecules that can be detected by infrared, ultraviolet or visible spectroscopy or by antibody interactions or by electron spin resonance. Biotin is another reporter molecule that can be detected by labeled avidin. Biotin could also be used to attach targeting groups.

EXPERIMENTAL SECTION

Example 1

Selection for Phage Persisting in Blood

We studied the interaction of displayed peptides with blood constituents using a T7 phage display library based on the Novagen T7Select415-1 vector. Each phage particle displayed 415 copies of a corresponding peptide at the carboxy-terminus of all copies of the phage coat protein 10B (Novagen T7Select System Manual, 1996). The phage with displayed peptides mimicked fairly well the delivery vehicles with the peptide ligands linked to the vehicles through the peptide amino-termini.

We found that the titer of the T7 phage peptide library in the plasma of rats preinjected with $GdCl_3$ (to inhibit macrophages (Mizgerd, et al., J. Leukoc. Biol., 59:189–95. 1996)) decreased by 95–99% within 5 min after phage injection. The rapid decrease in the phage titer was not accompanied by phage accumulation in blood cells, liver, kidneys, spleen, lungs, heart and skeletal muscles (data not shown). Therefore, the phage appeared to be functionally inactivated in blood. This was confirmed by observing phage inactivation in rat serum in vitro. Typical recovery of phage after incubating phage library ($10^7$ pfu) with 100 μl of serum at 37° C. for 30 min was less than 1%.

In contrast to the phage library, wild-type T7 survived in vivo quite well. 15–20% of wild-type phage was recovered from plasma in 5 min after injection. Since the library phage and wild-type phage were different only in the structure of the carboxy-terminal part of their coat proteins (Novagen T7Select System Manual, 1996), this suggested that the inactivation of the library was associated, at least in part, with the structure of the protein 10B C-termini displaying peptides.

The mechanism of phage inactivation by blood constituents was studied using non-selected phage and the phage selected for persistence in the blood of rats over 60 min in an infectious state. The phage yield from the plasma of rats in the $1^{st}$ round of selection was approximately 0.01%. The yield rose to approximately 15% in the $2^{nd}$ round and stayed around this level through 3 following rounds of selection. After the $5^{th}$ round, 33 individual clones were isolated and sequenced. All sequenced clones displayed peptides with either a K or an R residue at the carboxy-terminus (Table 1, A and B). These clones were hence designated K+ and R+clones (K+/R+as a class), respectively. Besides the carboxy-terminal K and R residues, there appeared to be preference for certain amino acid residues at other peptide positions (marked in bold in Table 1, A and B). Non-selected phage were randomly isolated from the initial library and divided into K+/R+ and K-JR-clones (Table 1, C and D).

TABLE 1

Primary structure of selected and non-selected T7 phage clones.

| Clone | Peptide |
|---|---|
| A. Selected K+ Phage | |
| 19-4 | QVTK |
| 19-5 | AK |
| 19-6 | VVVESVPK |
| 19-7 | ARPVQK |
| 19-9 | GRLK |
| 19-15 | AFTNK |
| 19-16 | VTPQVK |
| 19-17 | AVK |
| 19-18 | DNTPKTK |
| 19-19 | SLK |
| 19-20 | HRPKEGGKPALK |
| 19-22 | RTNPKVK |
| 19-24 | TTRTPK |
| 19-25 | NNAQGARVK |
| 19-28 | MATVK |
| 19-29 | KLRMK |
| 19-30 | GVREPK |
| 19-31 | PTIK |
| 19-32 | SRASVKGSTK |
| 19-33 | IK |
| 19-35 | TK |
| 19-37 | KTK |
| 19-38 | RKPQK |
| 19-40 | KVREK |
| B. Selected R+ Phage | |
| 19-1 | GGR |
| 19-3 | ASRVR |
| 19-10 | RER |
| 19-11 | KSGGPAER |
| 19-13 | RRRNFER |
| 19-14 | MDSMSNTPNGSER |
| 19-21 | PSSQQAQR |
| 19-36 | KNMR |
| 19-39 | QR |
| C. Non-Selected K+/R+ Phage | |
| IL-2 | AVK |
| IL-7 | QLVRVISR |
| IL-15 | R |
| L5-3 | NSR |
| L5-7 | RKSLR |
| L5-10 | RK |
| D. Non-Selected K-/R- Phage | |
| IL-1 | IEFSG |
| IL-8 | * |

TABLE 1-continued

Primary structure of selected and non-selected T7 phage clones.

| Clone | Peptide |
|---|---|
| IL-9 | MVLPFQQTVA |
| IL-11 | QSANI |
| IL-14 | KIPY |
| IL-16 | LPSGG |
| IL-20 | YNAKTDRG |
| IL-21 | L |
| IL-23 | KTNVEKGPM |
| IL-27 | NSNAGLENH |
| IL-32 | IQL |
| L5-1 | ME |
| L5-8 | MVRRV |
| L5-9 | LSARAP |
| E. Selected Y+ Phage | |
| 32-2 | RSYR |
| 32-3 | QESRTETDSQYLA |
| 32-5 | QGDYT |
| 32-16 | MQYS |
| 32-17 | YRA |
| 32-22 | YGPQQ |
| 32-24 | VDY |
| 32-26 | GKGKTDDPRYQKFT |
| 32-28 | AATGSDQGLNKAY |

Legend to Table 1: Bold letters that designate frequently occurring amino acid residues in K+/R+ (A and B) and Y residues in Y+ (F) peptides. "*" designates stop-codons.

Both selected and non-selected K+/R+ phage persisted in plasma in infectious state much longer than K-/R- phage (FIG. 1A). None of the tested K-/R- clones, featuring altogether 10 different carboxy-terminal peptide residues (Table 1D), showed significant presence in plasma (FIG. 1A). Therefore, the persistence of K+/R+ phage in circulation was mainly due to the presence of a K or an R residue at the peptide carboxy-terminus. K+/R+ clones, in contrast to K-/R- clones, also showed a high level of survival in serum (Table 2, A, D and G). This suggested a common mechanism for K+/R+ phage protection in vivo and in vitro.

TABLE 2

The effect of various conditions on phage inactivation in vitro.

| | Clone | Serum Treatment | Additions | % Phage Survival* |
|---|---|---|---|---|
| A. | K+ | none | none | 52.0 ± 19.6 |
| B. | K+ | Lysine-Sepharose | none | 1.8 ± 2.1 |
| C. | K+ | Lysine-Sepharose | CRP | 53.5 ± 19.8 |
| D. | R+ | none | none | 44.5 ± 9.0 |
| E. | R+ | Lysine-Sepharose | none | 0.4 ± 0.5 |
| F. | R+ | Lysine-Sepharose | CRP | 37.0 ± 13.3 |
| G. | K-/R- | none | none | 0 |
| I. | K-/R- | Lysine-Sepharose | none | 0.3 ± 0.3 |
| J. | K-/R- | Lysine-Sepharose | CRP | 0.1 ± 0.3 |
| K. | K+/R+ | none | 200 mM PC | 0 |

Legend for Table 2: [* mean±standard deviation. The effect of CRP on the survival of K+/R+ phage in Lysine-Sepharose-treated serum was assessed by incubating 10 µl ($10^6$ pfu) of phage with 300 pl of serum supplemented with 10 µg of CRP. The total volume of the samples was adjusted to 500 µl with PBS/0.68 mM $CaCl_2$. The samples were incubated at 37° C. for 30 min, and examined for the presence of infectious phage by a plaque forming assay (Novagen, Novagen T7Select System Manual, 1996). The phage survival percentage was calculated using the data for 5 different clones with the same type of the protein 10B carboxy-terminus.]

Methods:

T7 Phage Peptide Display Library. The vector T7Select415-1 (NSSVDKLAAALE) (Novagen, Madison, Wis.) was employed to display random peptides (NSDGA(X)$_{20}$GAVKLAAALE) at the carboxy-terminus of all phage coat protein 10B molecules (Novagen T7Select System Manual, 1996). The expression of the second coat protein, 10A, was disabled (Novagen T7Select System Manual, 1996). The vector insert was generated from the oligonucleotide xxxGAATTCggacggtgcc (NNG/T)$_{20}$ ggggctggaAAGCTTxxxxcx, where N is any of the four nucleotides and xxx are the nucleotides added to the 3' and 5' ends in order to enhance the efficiency of restriction digestion. The oligonucleotide was made double-stranded with Klenow fragment, using a reverse primer xxocxx-AAGCTTtccagcccc. After EcoR I and Hind III restriction enzyme digestion, the insert was ligated into T7Select415-1 vector (Novagen T7Select System Manual, 1996). The vector was packaged (Novagen T7Select System Manual, 1996) and an aliquot of the packaging mixture was used to estimate the complexity of the library by a plaque forming assay as described below. The apparent complexity of the library was $10^8$. Packaged phage was amplified in a log phase 0.5 L culture of the BL21 E. coli strain at 37° C. for 4 hs. The cell debris was removed by centrifugation and the phage was precipitated with 8% polyethylene glycol (M.W. 8,000) (Novagen T7Select System Manual, 1996). Phage was extracted from the pellet with 10 mM Tris-HC1/1M NaCl/1 mM EDTA (pH 8.0) and stored in PBS containing 10% glycerol at −80° C. (Novagen T7Select System Manual, 1996). The amplified library used in selection experiments displayed only truncated peptides, 1–14 amino acid residues long, immediately at the 10B protein carboxy-terminus (Table 1). The clones with full-size peptide inserts were lost during amplification. UV-inactivated phage was prepared by irradiating 1 ml of phage ($10^{12}$ pfu/ml; PBS) in a well of a 6-well tissue culture plate pretreated with BSA for 15 min under constant stirring. A germicidal lamp (15W; Sylvania G . T8) positioned 8 cm from the sample served as a source of UV.

In Vivo Studies. Long-circulating T7 phage was selected using 180–200 g Sprague-Dawley female rats pre-injected with GdCl$_3$ (10 mg/kg body weight) (Mizgerd, et al., J. Leukoc. Biol., 59:189–95. 1996) a day before. The animals were anesthetized with Ketamine (80 mg/kg) and Xylazine (4 mg/kg) and $10^{10}$ pfu (plaque-forming units) of phage in PBS in the first or $10^9$ pfu in the following selection rounds were injected into a tail vein. After 60 min, 6 ml of blood were collected from two animals into 600 units of heparin (Elkins-Sinn, Inc.) and phage in plasma were amplified as above. Individual clones were analyzed by PCR cycle sequencing.

Persistence of phage in plasma was assessed by injecting $10^9$ pfu of phage into a tail vein. At specified time points, 100 μl blood samples were collected from a non-injected tail vein into 10 U of heparin on ice. Phage titers in blood samples on ice did not diminish over time. After centrifugation at 14,000 rpm for 5 min and 1–3×$10^3$ fold dilution of the samples with LB medium, the amount of infectious phage was determined using a plaque forming assay (Novagen T7Select System Manual, 1996). Briefly, 10 μl of diluted plasma were incubated with 250 μl of log phase BL21 E. coli cells for 5 min, mixed with 3 ml of 0.7% agar in LB medium and plated onto 1.5% agar in 10 cm plates. The plaques were allowed to develop overnight at room temperature or over 4 hs at 37° C. The total amount of circulating phage was calculated based on a 6.4 ml plasma volume for 200 g rats (Lee and Blaufox, J. Nucl. Med., 26:72–6. 1985). C activity was inhibited by pre-injecting rats intraperitoneally with 100 μg/kg of CVF (Calbiochem) 20 hs before the phage injection. In PC co-injection experiments, phage was injected in PBS containing 10 mM PC (Na salt).

Serum Preparation. Rat serum was prepared by clotting blood on ice. Lysine-Sepharose-treated serum was prepared by passing 3 volumes of serum through 1 volume of Lysine-Sepharose (Amersham Pharmacia Biotech) equilibrated with PBS/0.68 mM CaCl$_2$. Complement-grade human serum from Sigma (Cat.# S-1764) was reconstituted from lyophilized powder following supplier's protocol, filtered and adjusted to pH 7.4. Both rat and human sera were stored for several days on ice. CVF treatment of serum was conducted by pre-incubating serum with CVF (10.8 μg/ml) at 37° C. for 60 min.

Example 2

Complement Inactivation of Phage

Given the prominent role of complement (C) in neutralizing foreign particulate material in the blood (Sakamoto, et al., Nutrition, 14:391–8. 1998), it was hypothesized that K−/R− phage were inactivated by C deposition. Pre-injecting rats with cobra venom factor (CVF) blocked in vivo inactivation of K−/R− phage, confirming this assumption (FIG. 1B). CVF closely mimics C3 and forms an unregulated C3/C5 convertase, which leads to depletion of C3 and C5 in the blood and blocks further C action (Cochrane, et al., J. Immunol., 105:55–69. 1970). CVF treatment also increased recovery of the phage library from rat serum in vtro, from less than 1% to approximately 50%. A similar increase in phage recovery (40–60%) was obtained in vitro with individual K−/R− clones. Thus, the phage was inactivated both in vivo and in vitro through C activation. Furthermore, the phage recovery in vitro was increased to approximately 70% by addition to serum of 10 mM Mg/EGTA; suggesting C activation through the classical pathway (Forsgren, et al., J. Lab. Clin. Med., 85:904–12. 1975).

The phage library was also inactivated by human serum. The incubation of $10^7$ pfu of the phage library with 100 μl of human serum at 37° C. for 30 min typically resulted in phage recovery of less than 1%. The phage recovery increased to approximately 40% and 80% after treatment with CVF and Mg/EGTA, respectively. CVF-sensitive inactivation of the phage library was also observed in mice (manuscript in preparation). Therefore, the inactivation of T7 display phage by C is a common phenomenon for different species. Human serum was different from rat serum in that it inactivated K+/R+ phage as efficiently as K−/R− phage (phage recovery<1%).

Example 3

Inactivation of Phage Requires Natural Antibodies

C activation through the classical pathway is typically triggered by formation of multivalent antigen-antibody complexes (Forsgren, et al., J. Lab. Clin. Med., 85:904–12. 1975). The role of antibodies in T7 phage inactivation was determined by depleting serum of specific classes of immunoglobulins. The survival rate of phage library ($10^7$ pfu) in the serum depleted of IgM under routinely used conditions was 62 ±16% (mean±standard deviation, n=3), as compared to 1.1±0.3% in non-treated serum. The survival of phage in IgG-depleted serum increased to 16±4% and the depletion of IgA had no effect on the phage survival rate (0.9±0.3%). The phage survival rate increased to 80–90% when more vigorous immunodepletion of IgM was conducted.

The addition of depleted IgM back to the IgM-depleted serum significantly restored the ability of the serum to inactivate phage library. Only 14±5% of the phage survived under these conditions. The inactivation of phage was restored even more efficiently, decreasing the phage survival rate to 4±3%, with human plasma IgM from Calbiochem (Cat.#401799). The IgM was isolated, according to the manufacturer, by gel-filtration followed by DEAE chromatography at pH 6.8. IgM was eluted from DEAE-Sepharose by gradually decreasing the pH to 5.0 (Jehanli and Hough, J. Immunol. Methods, 44:199–204. 1981). Similarly prepared human myeloma IgM (Calbiochem Cat.# 401108) had no effect as the phage survival rate in reconstituted serum remained above 60%. Human plasma IgM from Sigma (Cat.# 1-8260) or Chemicon (Cat.# AG722) did not restore phage inactivation either. The corresponding phage survival rates were 68±13 and 74±10%, respectively.

The 2-D electrophoresis (O'Farrell, J. Biol. Chem., 250:4007–21. 1975) revealed that Calbiochem IgM had a wider range of isoforms and was far more acidic than Chemicon IgM. Non-reducing SDS polyacrylamide/agarose electrophoresis (Fazel, et al., Int. Immunol., 9:1149–58. 1997) showed that both preparations contained predominantly pentameric IgM. Fractionation of Calbiochem IgM on Sephacryl 300 HR or Sephacryl 400 HR (Amersham Pharmacia Biotec) demonstrated that the reconstitution activity was associated with the major IgM peak. Similar results were obtained with the IgM fractionated by ammonium sulfate precipitation or ion exchange chromatography on DEAE-Sepharose (data not shown). Therefore, the protein that restored phage inactivation activity to IgM-depleted serum appeared to be an acidic, predominantly pentameric form of IgM (Niles, et al., Proc. Natl. Acad. Sci., USA, 92:2884–8. 1995). The role of IgM in T7 inactivation was confirmed by comparing phage survival in vivo in C57BL/6J (control) and C57BL/6J Rag-1 (IgM-deficient) mice pre-injected with $GdCl_3$. The survival of phage in 30 min after injection ($10^8$–$10^9$) was 20–50 times higher in C57BL/6J Rag-1 mice than in C57BL/6J mice.

The effect of IgM or IgG depletion on phage inactivation indicated that the phage inactivation was mediated by natural antibodies whose appearance in the blood does not require the presence of the corresponding antigen (Lacroix-Desmazes, et al., J. Immunol. Methods, 216:117–37. 1998). Natural antibodies are represented by IgM (Lacroix-Desmazes, et al., J. Immunol. Methods, 216:117–37. 1998) and, to a smaller extent, by IgG (Yu, et al., J. Immunol., 157:5163–8. 1996). At least two IgM (or IgG) subunits must be simultaneously engaged in the antigen binding to initiate C activation (Cooper, Adv. Immunol., 37:151–216. 1985). Methods for Serum immunodepletion and reconstitution: Human serum was depleted of IgM, IgG or IgA by passing 1 ml of serum through 2 ml of Sepharose containing immobilized goat anti-human IgM (µ-chain-specific; Sigma Cat.# A-9935), Protein G (Sigma Cat.# P-4691) and goat anti-human IgA α-chain-specific; Sigma Cat.# A-2691), respectively. The serum was eluted from the columns with PBS and collected in the total volume of 2 ml. IgM was eluted from the column by Pierce Gentle Elution Buffer, dialyzed against PBS and concentrated using Centricon-100 units. The survival of phage in immunodepleted serum was evaluated after incubating 10 µl of phage library ($10^7$ pfu) with 200 µl of serum at 37° C. for 30 min. The survival of phage in reconstituted serum was assessed after incubating 10 µl of phage library ($10^7$ pfu) with 200 µl of IgM-depleted serum in the presence of exogenous IgM (0.5 mg/ml). The total sample volume was adjusted to 400 µl with PBS/0.8 mM $CaCl_2$.

Example 4

IgM Initiates Phage Inactivation by Binding to Displayed Peptides

To find the protein 10B determinant that bound IgM and caused C activation, we analyzed the survival in human serum of a series of phage clones with truncated 10B proteins (described in the legend to Table 3). Clone 20-6 had the shortest protein 10B and a high efficiency of survival in human serum (Table 3A). Using the approach described below for identification of the plasma protein that protects K+/R+ phage against C (FIG. 2C) we found that immobilized phage 20-6 did not bind a significant amount of any protein (data not shown). Nor was the resistance of clone 20-6 to C inactivation due to a particular primary structure of its 10B protein carboxy-terminus. We have found no clones with detectable resistance to C that would display peptides similar in structure to the clone 20-6 10B protein carboxy-terminus. The phage 20-6 coat protein 10B was, therefore, intrinsically resistant to C.

TABLE 3

Interaction of protein 10B truncated carboxy-termini with IgM in human serum.

| Clone | Coat protein carboxy-terminus | % Phage Survival * | % Phage Resistant to Immunoprecipitation* |
|---|---|---|---|
| A. 20-6 | AAGAVVFQ | 90 ± 9 | 90 ± 25 |
| B. Wild- | AAGAVVFKVE | 34 ± 6 | 126 ± 11 |
| C. 32-77 | AAGAVVFQS | 103 ± 8 | 86 ± 16 |
| D. 32-23 | AAGAVVFSQV | 54 ± 2 | 89 ± 9 |
| E. 32-56 | AAGAVVFQSE | <0.1 | 22 ± 3 |
| F. 15-28 | AAGAVVFQSGAA | <0.1 | 3 ± 3 |
| G. Display | AAGAVVFQSGVM LGDPNSDGA(X)$_{1-14}$ | <1 | 4 ± 2 |

Legend to Table 3: [* mean± standard deviation (n=3). Clones 32-23, 32-77 and 32-56 were isolated after the $1_{st}$, 3d and $4^{th}$ rounds of selection for phage surviving in human serum, respectively. Clone 15-28 was selected for its ability to accumulate in rat liver (data not shown) and the selection of clone 20-6 will be described elsewhere. Phage survival was assessed by incubating 10 µl of T7 phage (~$10^6$ pfu) with 100 µl of human serum at 37° C. for 30 min. Immunoprecipitation samples contained 10 µl of phage (~$10^5$ pfu), 2 µl of human serum, 10 µl of 20 mM EDTA and 18 µl of PBS. EDTA was used to block C activation (Forsgren, A., et. al. J Lab. Clin. Med 85, 904–912 (1975)). The samples were incubated at 37° C. for 30 min and then treated with 200 µl of immobilized (50% agarose slurry) goat anti-human IgM (Sigma Cat.# A-9935) or anti-human IgA (Sigma Cat.# A-2691) antibodies at 4° C. for 30 min. Agarose was precipitated by low-speed centrifugation and the percentage of phage resistant to immunoprecipitation was determined by titering phage in the supernatants. The recovery values for the phage treated with anti-IgM antibodies were normalized to the corresponding values obtained with anti-IgA antibodies used as control. The absolute recovery of phage treated with anti-IgA antibodies was around 100%.

About 90% of the coat protein in wild-type phage is represented by protein 10A and only 10% by protein 10B.

The wild-type protein 10A can be viewed as a protein 10B in clone 20-6 that has the carboxy-terminal Q substituted for KVE (Table 3B). Wild type T7 phage was quite resistant to C inactivation in human serum (Table 3B).

Clone 32-77 had one additional amino acid residue at the 10B protein carboxy-terminus relative to clone 20-6 and showed a similar efficiency of survival in human serum (Table 3C). Clone 32-23 (Table 3D) was different from clone 20-6 in that it had one additional amino acid residue (S) inserted between F and Q residues and another (V) located at the carboxy-terminus. Clone 32-23 survived in serum quite well, although less efficiently than clones 20-6 and 32-77 (Table 3D). Clone 32-56 (Table 3E) had two additional amino acid residues at the carboxy-terminus of 10B protein relative to clone 20-26 and was almost completely inactivated in human serum (Table 3E). The strong inactivation of clone 32-56 was somewhat unexpected, as it was isolated after 4 rounds of selection for survival in human serum. The 10B protein in clone 15-28 (Table 3F) had two additional amino acid residues (SG) from the protein 10B sequence followed by three others (AAR) of unknown origin. This clone was inactivated in human serum (Table 3F).

Thus, the appearance of phage sensitivity to C correlated with minor changes in the structure of the protein 10B carboxy-terminus. In particular, the addition of as few as two amino acid residues (clone 32-56) to the protein 10B carboxy-terminus in C-resistant clone 20-6 was sufficient to render this phage C-sensitive. This is consistent with the fact that all tested K−/R− clones with non-truncated coat proteins were liable to C inactivation in rat serum. The survival of clones with truncated 10B proteins in serum may be explained by insufficient exposure of the C-termini of these proteins to the plasma constituents required for phage inactivation.

The minor changes in the structure of the protein 10B carboxy-terminus that rendered the phage liable to C inactivation also caused the recognition of phage by IgM. The efficiency of immunoprecipitation for C-resistant clones 20-6, 32-77 and 32-23 and wild-type phage in the samples treated with immobilized anti-IgM was almost as low as that in control samples treated with anti-IgA (Table 3, A-D). In contrast, the efficiency of immunoprecipitation with anti-IgM for C-sensitive clones 32-56 and 15-28, as well as for the phage library in general, was quite significant (Table 3, E-G). Therefore, the inactivation of phage by C was apparently mediated by binding of IgM to the carboxy-terminal sequence of the protein 10B.

Example 5

Peptide-Specific Natural Antibodies

The basis for IgM binding to disparate 10B protein carboxy-terminal sequences in different clones was elucidated by studying the ability of phage inactivated by UV-irradiation to rescue the phage with identical or different displayed peptides from C inactivation. For example, the recovery of phage IL-14 (Table 1D and FIG. 1A, K−/R− phage) in vivo dramatically increased if the phage ($10^9$ pfu) was co-injected with an excess ($10^{12}$ pfu) of the same phage inactivated with UV irradiation (FIG. 1B, IL-14/UV IL-14). The UV-inactivated phage IL-14 did not, however, rescue phage IL-16 (Table 1D and FIG. 1B, IL-16/UV IL-14). Other tested combinations of clones (Table 1D) gave results very similar to those shown in FIG. 1B. In addition to IL-16, UV-inactivated IL-14 did not rescue IL-1 and IL-20.

UV-inactivated IL-1 rescued IL-1 but did not rescue IL-14 and IL-16. Similarly, UV-inactivated IL-21 rescued IL-21 but did not rescue IL-8 and IL-32. UV-inactivated phage also rescued live phage with identical but not with different peptides in human serum (data not shown).

Moreover, most phage with the peptides that differ from each other only in one amino acid residue will compete with each other in the inactivation assay only to a very limited extent (Table 4).

| Variable Amino Acid Residue position | UV Phage Peptide | Live Phage Peptide | Survival of Live Phage, % (mean ± SD) |
|---|---|---|---|
| −1 | DGAI | DGAI | 89 ± 24 |
| −1 | DGAI | DGAA | 4 ± 2 |
| −2 | DGALAS | DGALAS | 103 ± 5 |
| −2 | DGALAS | DGALSS | 25 ± 22 |
| −2 | DGADL | DGADL | 82 ± 1 |
| −2 | DGADL | DGANL | 5 ± 6 |
| −3 | DGAGVY | DGAGVY | 74 ± 15 |
| −3 | DGAGVY | DGALVY | 20 ± 12 |

Table 4. The specificity of the PSNA-peptide binding was evaluated by comparing the survival of phage ($10^5$ pfu) in rat serum (20 μl) in the presence of an excess of UV-inactivated phage ($10^{10}$ pfu) with the peptide that was either the same or different just in one amino acid residue. The total volume of the sample was adjusted to the 240 μl with PBS. The samples were incubated at 37° C. for 30 min and the percentage of surviving live phage was determined by a plating assay.

Example 6

A Serum Factor Prevents K+/R+ Phage Inactivation

Serum passed through Lysine-Sepharose (that mimics peptide carboxy-terminal K residues (Deutsch and Mertz, Science, 170:1095–6. 1970) efficiently inactivated K+/R+ phage (Table 2, B and E), suggesting that K+/R+phage was protected against C by a serum compound bound to carboxy-terminal K or R amino acid residue. The protective compound was eluted from Lysine-Sepharose by either 0.5 M NaCl or 2 mM EDTA, as judged from the restoration of the serum protective activity with respect to K+/R+ phage by these eluates (Table 2, C and F). As expected, Lysine-Sepharose also bound plasminogen (Deutsch and Mertz, Science, 170:1095–6. 1970). Plasminogen was eluted by ε-aminocaproic acid (ε-ACA) (Deutsch and Mertz, Science, 170:1095–6. 1970) and had no protective effect on phage (data not shown).

Example 7

Identification of the Serum Protective Factor

The only major polypeptide eluted by 0.5 M NaCl or 2 mM EDTA had a molecular weight of approximately 30 kDa (FIG. 2A, lanes 1 and 2, respectively). The polypeptide was identified by microsequencing (Kendrick Laboratories, Madison Wis.) as CRP that is normally present in rat serum at the concentration of 0.3–0.5 mg/ml (de Beer, et al., Immunology, 45:55–70. 1982). Immunoblot analysis confirmed that the eluted protein was CRP (FIG. 2B, lane 1).

The binding of CRP to Lysine-Sepharose could be explained by a certain similarity between the lysine residues attached to Sepharose through lysine α-amino groups and the predominant CRP ligand, phosphorylcholine (PC). Like PC, the carboxy-terminal lysine contains two oppositely charged compact groups separated by a short aliphatic chain. The carboxy-terminal arginine shares this likeness. CRP is eluted from Lysine-Sepharose as a sharp peak with 1 mM PC in PBS/0.68 mM $CaCl_2$, which lends support to this notion (data not shown). The elution of CRP by EDTA from Lysine-Sepharose is consistent with the strict $Ca^{2+}$-dependence of CRP-PC interaction (Volanakis and Kaplan, Proc. Soc. Exp. Biol. Med., 136:612–4. 1971), PC reduced the protection of K+/R+ phage both in vivo and in vitro, thereby confirming the role of CRP as a K+/R+ protection agent (FIG. 1D and Table 2K, respectively). The $IC_{50}$ determined for K+19/16 and R+19/14 clones in vitro was approximately 50 $\mu$M. Direct interaction between CRP and K+/R+ phage was shown with the phage immobilized on Affi-Gel 15. Immobilized K+/R+ phage, but not K−/R− phage, bound a substantial amount of serum protein that was eluted from the column by $\epsilon$-ACA (FIG. 2C). SDS-PAGE showed that the major protein bound to K+ or R+ phage had the electrophoretic mobility identical to that of CRP (FIG. 2A, lanes 3 and 4). The identification of this protein as CRP was confirmed by the Western blot analysis (FIG. 2B, lanes 2 and 3). No binding of CRP to K−/R− phage or a mock column was detected. The binding of CRP to K+/R+ phage was $Ca^{2+}$-dependent and did not take place in the presence of $Mg^{2+}$ alone (data not shown). The presence of multiple CRP molecules on surface of K+/R+ phage could provide steric protection against C-mediated inactivation. The role of CRP in protecting K+/R+ phage against C is consistent with the lack of protection for K+/R+ phage in human serum which normally contains little CRP.

The concentration of CRP in many species, humans included, is dramatically increased as a result of an acute phase reaction (Szalai, et al., Immunol. Res., 16:127–36. 1997). The exact role of CRP in vivo is unclear. The functions ascribed to CRP include modulation of the immune cell behavior, participation in killing infectious agents and clearance of cellular debris(Szalai, et al., Immunol. Res., 16:127–36. 1997). The ligands that competitively interact with the CRP PC-binding sites include phosphate monoesters (Volanakis and Kaplan, Proc. Soc. Exp. Biol. Med., 136:612–4. 1971), certain galactans (Volanakis and Narkates, J. Immunol., 126:1820–5. 1981, Culley, et al., J. Immunol., 156:4691–6. 1996), lipoproteins and lipids (Pepys, et al., Int. Rev. Exp. Pathol., 27:83–111. 1985), immobilized laminin and fibronectin (Tseng and Mortensen, Exp. Cell. Res., 180:303–13. 1989) and cationic polymers and proteins (Dougherty, et al., Mol. Immunol., 28:1113–20. 1991, Du Clos, et al., J. Biol. Chem., 266:2167–71. 1991). Specific binding of CRP in situ to snRNPs (Pepys, et al., Clin. Exp. Immunol., 97:152–7. 1994) and covalent binding in vivo to C components C3 and C4 have been reported (Wolbink, et al., J. Immunol., 157:473–9. 1996).

Carboxy-terminal K and R residues are readily generated in vivo at the cell or extracellular matrix surface by trypsin-like proteases (Liotta, et al., Cancer Res., 41:4629–36. 1981). The binding of CRP to such carboxy-termini could modulate the blood exposure of new protein epitopes created by extensive proteolysis. The CRP binding to proteolytic products might also play a role in the clearance of cellular debris released from dying cells (Du Clos, et al., J. Biol. Chem., 266:2167–71. 1991, Pepys, et al., Clin. Exp. Immunol., 97:152–7. 1994, Du Clos, et al., J. Immunol., 141:4266–70. 1988, Jewell, et al., Mol. Immunol., 30:701–8. 1993).

Discussion Concerning CRP's Role in Phage Protection: CRP belongs to the pentraxin family of pentameric proteins highly conserved among different mammalian species. It was originally named because it binds the C-polysaccharide of *pneumococcus* and it was eventually discovered that it binds the phosphocholine moiety on the C-polysaccharide. It requires calcium for this binding. CRP can bind the phosphocholine headgroups of phospholipids such as phosphatidylcholine or sphingomyelin but not in "intact" bilayers (Richards, et al., Proc. Natl. Acad. Sci USA, 74:5672–5676. 1977). Galactosyl residues in the presence of accessible phosphocholine groups enhance CRP binding, C1q binding, and C4 activation, which raises concerns about using galactosyl groups for hepatocyte targeting of liposomes (Volanakis and Narkates, J. Immunology, 126:1820–1825. 1981). Similarly, exposure of galactosyl groups on erythrocyte membranes by desialation activates C by CRP binding (Pepys and Baltz, Advances in Immunology, 34:141–212. 1983).

Human CRP is a major acute phase reactant that is widely used for detecting inflammation- and injury-related conditions(Szalai, et al., Immunologic Research, 16:127–36. 1997). CRP is constitutively elevated in rats. The exact role of CRPin vivo is unclear. The functions ascribed to CRP include modulation of immune cell behavior, participation in killing infectious agents and clearance of cellular debris (Szalai, et al., Immunologic Research, 16:127–36. 1997) (Barna, et al., Cancer Research, 44:305–310. 1984). The ligands that competitively interact with the CRP PC-binding site include phosphate monoesters (Volanakis and Kaplan, Proceedings of the Society for Experimental Biology & Medicine, 136:612–4. 1971), certain galactans (Volanakis and Narkates, J. Immunology, 126:1820–1825. 1981, Culley, et al., Journal of Immunology, 156:4691–6. 1996), lipoproteins and lipids(Pepys, et al., International Review of Experimental Pathology, 27:83–111. 1985), immobilized laminin and fibronectin (Tseng and Mortensen, Experimental Cell Research, 180:303–13. 1989) and cationic polymers (polylysine, protamine, poly-arginine) and proteins (Du Clos, et al., Journal of Biological Chemistry, 266:2167–71. 1991, Dougherty, et al., Molecular Immunology, 28:1113–20.1991) (Siegel, et al., J. Exp. Med., 142:709–721. 1975). Thus, CRP could have important effects on a number of non-viral vector systems. Specific binding of CRP in situ to snRNPs (Pepys, et al., Clinical & Experimental Immunology, 97:152–7. 1994) and covalent binding in vivo to C components C3 and C4 have been reported (Wolbink, et al., Journal of Immunology, 157:473–9. 1996).

The exact mechanism by which CRP protects Lys+/Arg+ phage against C-mediated inactivation remains to be established. Simple steric protection could be achieved just due to the presence of multiple CRP molecules on the phage surface. Bound CRP may also directly inhibit C action at the phage surface. Although CRP activates the C classical pathway (Kaplan and Volanakis, Journal of Immunology, 112:2135–47. 1974, Siegel, et al., Journal of Experimental Medicine, 140:631–47. 1974), it also inhibits the activation of the alternative and lectin pathways on the surface to which it binds. The inhibition is associated with increased C regulatory protein H binding to C3b (Suankratay, et al., Clinical & Experimental Immunology, 113:353–359. 1998, Mold, et al., J. Immunol., 133:822–825. 1984). Perhaps, CRP's inactivation of the alternative pathway is predominant and protects the phage from C inactivation.

An important aspect of the finding that protein C-reactive protein binds to C-terminal Lys and Arg residues is a frequent occurrence of such C-termini in the blood. They are generated at the cell or extracellular matrix surface by blood trypsin-like proteases such as thrombin and plasmin (Liotta, et al., Cancer Research, 41:4629–36. 1981). The binding of CRP to such C-termini could regulate the interaction of C and immune system cells with potentially immunogenic new epitopes(Szalai, et al., Immunologic Research, 16:127–36. 1997, Suankratay, et al., Clinical & Experimental Immunology, 113:353–359. 1998). The CRP binding to proteolytic products might also play a role in the clearance of nuclear debris released from dying cells (Du Clos, et al., Journal of Biological Chemistry, 266:2167–71. 1991, Pepys, et al., Clinical & Experimental Immunology, 97:152–7. 1994, Du Clos, et al., Journal of Immunology, 141:4266–70. 1988, Jewell, et al., Molecular Immunology, 30:701–8. 1993). The abundance of Lys and Arg in nuclear proteins makes proteolytic generation of C-terminal Lys and Arg aa particularly easy. It is noteworthy that the nuclear protein Sm-D that binds to CRP in solution(Jewell, et al., Molecular Immunology, 30:701–8. 1993) and is a constituent of snRNPs recognized by CRP in situ (Pepys, et al., Clinical & Experimental Immunology, 97:152–7. 1994) has a Lys at the C-terminus. A C-terminal Lys is also present in histone H1 that is required for CRP binding to chromatin in vitro(Du Clos, et al., Journal of Immunology, 141:4266–70. 1988). It should also be mentioned that all of the peptides that corresponded to nuclear protein sequences and bound to CRP in vitro incidentally contained a Lys or Arg at the C-terminus (Du Clos, et al., Journal of Biological Chemistry, 266:2167–71. 1991, Jewell, et al., Molecular Immunology, 30:701–8. 1993).

The observed selection of exclusively Lys+/Arg+ clones resulted from the combination of used selection conditions and make-up of the original library. Lys+/Arg+ clones were initially present in the library since there was no pre-selection against truncated peptides resulting from stop-codons. The selection of Lys+/Arg+ clones was promoted as well by macrophage suppression and a long phage circulation time. Using different conditions, we were able to select Lys−/Arg− phage that persisted in vivo (see below). Thus, the T7 display system used herein appears to have wide applicability with respect to selecting peptide determinants recognized by blood proteins in vivo.

Methods for Isolation and testing of CRP. 100 ml of filtered, Sprague-Dawley rat serum (Pel-Freez Biologicals) was applied onto a 25-ml column of Lysine-Sepharose equilibrated in PBS/0.68 mM $CaCl_2$. The column was washed with 10 volumes of PBS/0.68 mM $CaCl_2$ and CRP was eluted with 2 mM EDTA in PBS. CRP was dialyzed against PBS, concentrated and stored at −20° C. CRP-enriched protein fraction eluted by 0.5 M NaCl was prepared using a plasminogen isolation protocol[21].

Methods for Affinity isolation of the serum protein protecting K+/R+ phage against Phage was immobilized on Affi-Gel 15 (Bio-Rad) following supplier's protocol. $10^{13}$ pfu of phage in 3 ml of 50 mM MOPS (pH 7.5) were incubated with 4 ml of settled gel overnight at 4° C. under constant mixing. The column was washed with 10 volumes of 10 mM Tris-HCl/1M NaCl/1 mM EDTA/ (pH 8.0) and 10 volume of PBS. 1 ml of settled gel contained 60–120 μg of phage protein. Rat serum (3 ml) was applied onto a column (4 ml) equilibrated in PBS/0.68 mM $CaCl_2$. The column was washed with PBS/0.68 mM $CaCl_2$ (8 volumes) and phage-bound protein was eluted with 2–20 mM ε-ACA in PBS/0.68 $CaCl_2$. 1.5 ml fractions were collected. Protein was determined by a BCA assay (Pierce). The amount of eluted protein was normalized to the amount of phage protein on the column, taking R+ phage as a standard.

Example 8

Selection for Phage Persisting in Human Serum

To compare the survival strategies of phage in sera from different species, we also selected for phage that survived in human serum. $10^9$ pfu of phage library (50 μl) was incubated with 1 ml of human serum (pH 7.4) at 37° C. for 30 min and amplified as described above.

The phage survival rate in the $1^{st}$ round of selection was less than 1%. The survival rate rose to about 100% in the $2^{nd}$ round and reached approximately 35% in the $5^{th}$ round of selection. The sequencing after the $1^{st}$ round of selection revealed a much higher than expected (24 vs. 3%, respectively) portion of clones with tyrosine (Y) residues in displayed peptides (Y+clones; Table 1E). Other peptides selected in the $1^{st}$ round of selection showed no similarity and were not included in further analysis.

All Y+ clones showed a relatively high rate of survival in human serum. The survival rate for different Y+ clones (Table 1F) was in the range of 25 to 60%. Sequencing of the clones after the $3^d$ and $4^{th}$ round of selection showed only a marginal increase in the percentage of Y+ clones (~30%), presumably due to a competing increase in the portion of clones with truncated 10B proteins (Table 3).

The differences in the structure of selected Y+ peptides suggested that the phage was protected against C via binding to plasma proteins rather than through assuming a specific "cryptic" conformation that is not recognized by natural antibodies. We found in our preliminary experiments with immobilized Y+ phage (clone 32-5, Table 1E) that the phage bound $α_2$-macroglobulin in human serum. Consistent with this observation the survival rate for selected Y+ clones in rat serum, that has a much lower level of $α_2$-macroglobulin, was approximately 5–10-fold lower than in human serum.

Example 9

Selecting Phage T7 Display Clones Persisting in the Blood of Rats Not Treated With Gadolinium The phage resistant to inactivation by C was selected surviving in rats with intact macrophages for 60 min. 15 individual selected clones were sequenced and all of them found to have the 10B protein truncated after $Q_{343}^9$ as a result of a single nonsense mutation in the serine codon (TCA⇒TAA). The selected phage did not display peptides as the mutation occurred upstream of the peptide cloning site. The sequenced clones belonged to three different genotypes, as judged from the different DNA sequences at the peptide cloning site. All clones were remarkably stable in the blood. Both with and without Gd pre-injection, the efficiency of the live phage recovery from plasma remained at the same level, in the range of 80–100%, for at least 30 min after phage injection. Approximately 4% of the injected phage could be recovered from the liver when the animals were perfused 5 min after phage injection. The presence of phage in the liver might be due to incomplete perfusion. The spleen, lungs and kidneys showed only trace phage accumulation. The persistence of clones with different genotypes in the blood at the same level pointed to the importance of the 10B protein truncation shared by all clones for phage survival. The contribution of other, undetected mutations into phage survival could not be ruled out but, even if present, was very limited. Neither in these nor in all following experiments did we detect any phage with a significant rate of survival and no obvious changes in the carboxy-terminal portion of the 10B protein. Therefore, the inactivation of the T7 phage library in rats was almost exclusively, if not entirely, driven by the structure of the 10B protein carboxy-terminus.

Affinity purification of an IgM species that bind specific T7 phage. Experimental design: To elucidate more exactly the role of IgM in peptide-dependent phage inactivation, we will study if there are indeed different classes of IgM that recognize different peptides. An alternative might be the existence of some other proteins that bind different classes of peptides and interact with the same class of IgM that activates complement. The specificity of an IgM species will also be confirmed.

Methods: T7 phage from the clone IL-14 (DGAKIPY) and two other clones, IL-13 (DGAVAYPPMLPVLHGSLARL) and IL-20 (DGAYNAKTDRG), that were not protected by an excess of UV-inactivated IL-14 will be immobilized on pre-activated Affi-Gel-10 by incubating phage with Affi-Gel overnight at 4° C. with end-over-end mixing. The resin will be washed with high-salt phage extraction buffer followed by Pierce Gentle Elution Buffer to eliminate a free phage contamination. Human or rat serum adjusted to the pH of 7.4 will be passed through the column with immobilized phage at 4° C. and the column will be washed with 5–10 volume of cold PBS containing. The serum proteins that bound to the immobilized phage will be eluted with Pierce Gentle Elution buffer. The eluate will be concentrated by centrifugation in Centricon 30 units and dialyzed against PBS. The resultant solution will be applied onto the affinity column containing goat antibodies (IgG) against human IgM. The column will be washed with 10 volume of PBS/0.5 M NaCl and IgM will be eluted with Pierce Gentle elution buffer. The eluted IgM will be concentrated, dialyzed against PBS and added to IgM-depleted serum to test its ability to reconstitute the inactivation by the serum of the phage clone that was used as an affinity ligand in the IgM isolation as compared to the phage clones with different peptides. Thus, the specificity of a particular IgM species will be determined.

Biotin Inactivation Methods

Biotinylation of T7 Phage: We have developed a novel system for selecting for phage that has been (Table 5)

TABLE 5

Infectivity of biotinylated T7 phage and its inactivation by neutravidin.

| Concentration of Biotin-LC-NHS, mM | Neutravidin treatment | Total number of phage plaques normalized to phage dilution | Inhibition of plaque-forming activity, % |
|---|---|---|---|
| 0 | | 23,800 | |
| | | – | – |
| 0.2 | – | 19,600 | |
| 0.2 | + | 72 | 99.63 |
| 0.5 | – | 15,600 | |
| 0.5 | + | 0 | 100 | internalized in cells. The idea is to lightly biotinylate the phage and inactivate it with neutravidin. If the phage has been internalized then it will be inaccessible to neutravidin and remain infectious. T7 phage can be biotinylated with only a small loss in its infectivity and this infectivity can be suppressed by neutravidin. T7 was labeled with Biotin-LC-NHS (Pierce), incubated with neutravidin (Pierce) and plated as recommended by the manufacturer (Novagen).We found that the interaction between the phage surface-onjugated biotin and free neutravidin can be used as an efficient inactivation "switch" with T7 phage display libraries. The treatment of T7 with 0.5 mM Biotin-LC-NHS resulted in very strong inhibition of phage infectivity by neutravidin. The inhibition of phage plaque-forming activity caused by the labeling procedure itself was 30–35% (for 0.5 mM Biotin-LC-NHS).

To show the accessibility of non-internalized, endothelium-attached phage to neutravidin, we used leg muscle as a model. After intravascular injection of biotinylated T7 phage library, the leg muscle was perfused with either PBS or PBS+ neutravidin. In muscles that were perfused with neutravidin, 80% of muscle bound phage was inactivated.

Determination of whether peptides with amino termini invoke the same process. Experimental design: The peptides displayed on T7 phage are cloned into the C-terminal portion of the phage coat protein 10B and, therefore, have free C-termini. In order to study the interaction with serum of the peptides that have free N-termini, we will use peptide libraries displayed on phage M13. In M13 peptide libraries, the peptides are cloned into the N-terminal portion of the phage coat proteins pIII or pVIII.

Methods: M13 libraries that display peptides in pIII (Bio-Labs) or pVIII (courtesy of G.Smith, University of Missouri) proteins and that have complexity around $10^9$ are used. Commercially available libraries from New England Bio-Labs have 7 and 12 amino acid residue long peptides. The f88-4 library from the Smith lab has 15 amino acid residue long peptides in pVIII (appr. 300 copies per phage particle). The libraries are incubated in mouse serum essentially as described above for T7 phage and the surviving phage is measured by a plating assay.

All tried M13 phage display libraries are inactivated by both human and rat serum. $10^6$ pfu of phage is inactivated by 100 $\mu$l of serum during the incubation at 37° C. for 30 min by 98–99%. A co-incubation of live phage with UV-inactivated phage ($10^{10}$ pfu prior to inactivation) of the same type rescues the majority of live phage.

The role of displayed peptides in phage inactivation is determined by co-incubating live library with UV-inactivated vector phage or wild-type M13 phage. The phage inactivation caused by the recognition of displayed peptides by specific natural antibodies can not be offset by the presence of an excess of wild-type phage coat proteins. The rescue of phage with displayed peptide by an excess of inactivated wild-type phage indicates that the phage is inactivated due to the interaction of serum constituents with wild-type proteins. On the other hand, the rescue of phage with displayed peptide by an excess of inactivated phage with displayed peptides only indicates that the phage is inactivated due to the interaction of serum constituents with displayed peptides.

Prolonged Circulation of Lys+/Arg+ Phage in Rats NOT Treated With Gadolinium

Although the Lys+/Arg+ phage were obtained by performing the selections in rats treated with gadolinium, they had significantly prolonged circulation in rats not treated with gadolinium. Several percent of injected Lys+/Arg+ phage could be recovered from rat plasma in an infectious state 5 min after injection. Almost no infectious Lys−/Arg− phage was recovered from plasma under these conditions.

Although, the actual circulation time of lys+/arg+ phage is relatively short compared to sterically-stabilized liposomes, their prolonged circulation is very significant for the following reasons. One, the lys+/arg+ phage have a blood circulation time that is more than 1,000-fold above the non-selected phage given that almost all of the phage is inactivated by 5 minutes. In comparison, PEG increases the circulation times of liposomes approximately hundred-fold. One needs to appreciate that the baseline for phage inactivation is different than that for liposomes which are inherently more stable in the blood than phage. Two, the fast, almost instant inactivation of most T7 clones in blood is, in fact, a very important feature of our selection system as it provides low background and short incubation times for selection of weak protein-phage interactions. Three, a relatively short circulation time of CRP-protected phage appears to be due to non-specific, concentration-independent phage inactivation/clearance. A thousand-fold increase in the amount of injected Lys+ phage had no effect on the percentage of live phage in the blood. In contrast, a thousand-fold increase in the amount of injected Lys– (not recognized by CRP) phage resulted in a dramatic increase in the survival of this phage in the blood. The survival of Lys– phage under these conditions was quantitatively very similar to that of Lys+ phage. Further increase in the amount of Lys– injected phage had no effect on the survival percentage. These results indicate that the circulation time of our selected phage is quite close to the maximum that can be obtained with this system. Artificial delivery vectors bearing the lys+/arg+ peptides may not be subject to this non-specific inactivation/clearance.

Selection of Phage Clones Resistant to Human Complement Inactivation

The binding and precipitating properties of CRPs from different species show certain. Further studies are necessary to extend our initial findings in the rat serum to human serum. "Lysine–/arginine–" phage are 100% inactivated by "normal" human serum containing just trace amounts of CRP. The extent of inactivation by human serum is comparable to that by rat serum Therefore, the inactivation of T7 phage by serum is a universal phenomenon, not confined to a particular species. Since human serum is naturally low in CRP (<10 µg/ml except during an acute phase response), we reasoned that selections in human serum would yield serum resistant "lys–/arg–" clones containing novel peptide sequences not obtained from the rat studies.

Selection of peptides that confer resistance on T7 phage against human complement was carried out using pooled commercial "complement grade" serum from Sigma (Cat. # S1764) and a new T7 peptide library containing 1–13 amino acid long linear peptides. The selection was performed under relatively "mild" selection pressure, using a relatively large phage/serum ratio. Lyophilized serum was reconstituted with water and filtered through a 0.22 µm filter prior to use. $10^9$ pfu of theT7 library in 200 µl of PBS were incubated with 1 ml of serum for 30 min and complement-resistant phage was amplified in a 0.5 L log culture of BL 21 E. coli. Amplified phage was isolated and the procedure was repeated 2 more times using the same conditions. 30 individual clones were isolated from the selected phage population, sequenced and grouped according to certain consensus residues (Table 5).

An obvious trait shared by many selected peptides was the high frequency occurrence of Ser and Thr residues near the C-terminus. 6 clones particularly stood out in that they had double or triple cysteins at the C-terminus. All other clones are presented in Table 5 according to the position of Ser/Thr residues in the corresponding peptides.

Table 5. Peptide sequences of the 30 individual clones that were obtained after selection for resistance to inactivation by human serum. The clones were divided into A-F groups according to the following criteria A. Peptides with double or triple Ser residues at the C-terminus, B. Peptides with single Ser residues at the C-terminus; C. Peptides with a Ser residue at the –2 position; D. Peptides with a Ser residue at the –3 position; E. Peptides containing Ser or Thr residues at any other but C-terminal, –2 or –3 positions; F. Peptides that do not contain Ser and Thr residues. Ser and Thr residues are shown in bold. The linker portion of 10B protein upstream of random peptides (10B) is underlined

*Clones 24-1 and 24-24 are genetically different (i.e., non-coding sequences are different).

TABLE 5

Clones selected for resistance against inactivation by human serum

A. Multiple COOH Ser

| | |
|---|---|
| 24-1 | DGALSS* |
| 24-10 | DGAHSSS |
| 24-11 | DGASNLSS |
| 24-16 | DGAARNTLSS |
| 24-21 | DGAAISSDGFINQSS |
| 24-24 | DGALSS* |

B. Single COOH Ser

| | |
|---|---|
| 24-15 | DGAALAS |
| 24-22 | DGAWS |

C. Ser at –2 Position

| | |
|---|---|
| 24-3 | DGANSP |
| 24-8 | DGASSV |
| 24-12 | DGASDRGNEEMSF |

D. Ser at –3 Position

| | |
|---|---|
| 24-6 | DGAMSPL |
| 24-14 | DGAVPSVSSPSIG |
| 24-23 | DGASGPSVG |
| 24-27 | DGATTSLG |
| 24-28 | DGSQM |

E. Ser or Thr/Not COOH

| | |
|---|---|
| 24-4 | DGAPSLSVGG |
| 24-5 | DGATTVDNM |
| 24-7 | DGANLVSGTRLD |
| 24-9 | DGATG |
| 24-17 | DGATTQTAY |
| 24-18 | DGASNLPL |
| 24-19 | DGAATRGR |
| 24-25 | DGASKKTVLAMNPR |
| 24-30 | DGATHGSEVA |

F. No Ser or Thr

| | |
|---|---|
| 24-2 | DGAVPL |
| 24-13 | DGARA |
| 24-20 | DGAMVG |
| 24-26 | DGAVRRG |
| 24-29 | DGAALVL |

To evaluate the efficiency of selection, all selected clones were amplified and tested individually for survival in human serum. Individual clones were tested for survival in human serum by incubating 10 µl of T7 phage with 300 µl of reconstituted serum diluted with 190 µl of PBS. The incubation was carried out at 37° C. for 30 min and the efficiency of phage survival was estimated by plating as described earlier. Percentage of T7 phage recovered (X axis) equals (# of recovered phage /# of injected phage) X 100. $10^7$ PFU's were used. We found that all selected clones with double Ser residues at the C-terminus showed a significant resistance to complement inactivation (~15 to ~55 percent survival). Furthermore, the presence of double Ser right at the C-terminus appears to be critical for phage survival. Thus, clone 24-8 that displayed peptide SSV showed a low resistance to complement inactivation (<1% survival) despite the presence of Ser residues at –2 and –3 positions. In addition, it is not clear whether the presence of a single Ser residue at the C-terminus is sufficient to protect phage against complement. Out of two selected clones with a single Ser residue at the C-terminus, one was quite resistant to serum inactivation (24/15) while the other (24/22) was totally inactivated. It is necessary to examine further clones to determine the role of other residues on the ability of a single C-terminal Ser to confer resistance to human serum. A number of selected clones that showed resistance to complement inactivation did not have peptides with Ser residues at the C-terminus (Table 6). Most interestingly, this suggests that selected peptides protect phage against complement inactivation via different mechanisms.

TABLE 6

Selected peptides that confer on T7 resistance to complement inactivation and do not have C-terminal Ser residues. Peptides in columns A and B are grouped based on a certain amount of similarity in the primary structure of C-termini.

A.

| | |
|---|---|
| 24-6 | DGAMSPL |
| 24-18 | DGASNLPL |
| 24-29 | DGAALVL |

B.

| | |
|---|---|
| 24-19 | DGAATRGR |
| 24-26 | DGAVRRG |

C.

| | |
|---|---|
| 24-5 | DGATTVDNM |
| 24-17 | DGATTQTAY |
| 24-25 | DGASKKTVLAMNPR |
| 24-27 | DGATTSLG |
| 24-28 | DGSQM |

The exact mechanisms of phage protection by selected peptides are currently being studied. There are two possible mechanisms: one, the peptide binds a serum protein that prevents C inactivation, or the two Ser residues act like PEG and reduce all serum protein interactions. Our proposed methods of using phage affinity columns (see Exp Protocol section) will distinguish between these two hypotheses. If it should be the first mechanism, then the exact serum proteins that bind the phage and prevent C inactivation will be identified (Oust as we did with the identification of CRP for rat serum).

In addition, it appears that the C terminus carboxyl group plays an important role since acidification of the serum abrogates the protection of the above selected clones. Further selections in human serum with adjusted pH's are in progress.

Inactivation of phage display library by pup rat serum and the serum from gnotobiotic rats.

Serum from newborn rats did not inactivate phage to a significant extent. Only 7.7+/−5.6% of the input phage was inactivated as compared to 96.3+/−0.3% in the serum from adult rats. The inactivation of phage by the serum of new-born rats could be induced by adding to the samples 100 μg of IgM (purified as described above). The efficiency of phage inactivation increased under these conditions to 70.5+/−4%. This suggests that the peptide-specific IgM develops in the neonatal period. Serum from gnotobiotic rats in vitro and in vivo inactivated phage as effectively as the serum from control animals indicating that the appearance of "active IgM" is not induced by environmental agents.

Liver targeting and blood persistence of T7 phage with truncated proteins in rats We have identified a number of spontaneous mutations that occur around the site corresponding to the translation shift point from 10A to 10B protein reading frame. Most of these phage clones were selected due to their resistance to serum inactivation. Interestingly, we discovered that their targeting behavior in vivo showed a wide spectrum of behavior (FIG. 1).

Both clones 20/6 (FQ*) and 32/77 (FQS*) are relatively stable in the blood but differ substantially in their liver targeting (FIG. 1). The one additional C-terminus serine in 32/77 results in over 20% of the injected phage ending up in the liver. Clones 32/33 (FSQV) and #112 (FQSGVMLGDPN*) also target to the liver but are not as stable in blood. Clones 114 and T7 vector, shown for control purposes, are not stable in blood and can not be detected in liver liver. The overall impression from these experiments is that liver targeting is associated with the exposure of peptides on the phage surface, regardless of the peptide primary structure.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cell biology, chemistry, molecular biology, biochemistry or related fields are intended to be within the scope of the following claims.

We claim:

1. A process for selecting phage that are resistant to blood inactivation, comprising:
   a) mixing a blood component with a phage display library in vitro under phage inactivation conditions; and,
   b) selecting for phage which are resistant to inactivation by the blood component.

2. The process of claim 1 wherein selection comprises multiple rounds of selection.

3. The process of claim 1 wherein the phage display library comprises T7 phage.

4. The process of claim 1 wherein a variable part of the phage DNA sequence is identified.

* * * * *